(12) United States Patent
Hou et al.

(10) Patent No.: US 12,054,722 B2
(45) Date of Patent: Aug. 6, 2024

(54) RECOMBINANT NUCLEIC ACID MOLECULE BASED ON POINT MUTATION OF TRANSLATION INITIATION ELEMENT AND USE THEREOF IN PREPARATION OF CIRCULAR RNA

(71) Applicant: Purecodon (Hong Kong) Biopharma Ltd., Hong Kong (CN)

(72) Inventors: Qiangbo Hou, Suzhou (CN); Zonghao Qiu, Suzhou (CN); Yang Zhao, Suzhou (CN); Chijian Zuo, Suzhou (CN); Zhenhua Sun, Suzhou (CN)

(73) Assignee: Purecodon (Hong Kong) Biopharma Ltd., Hong Kong (CN)

( * ) Notice: Subject to any disclaimer, the term of this patent is extended or adjusted under 35 U.S.C. 154(b) by 13 days.

(21) Appl. No.: 17/871,434

(22) Filed: Jul. 22, 2022

(65) Prior Publication Data

US 2023/0279407 A1  Sep. 7, 2023

(30) Foreign Application Priority Data

Mar. 2, 2022 (CN) .......................... 202210200186.X

(51) Int. Cl.
  *C12N 15/67* (2006.01)
(52) U.S. Cl.
  CPC ........ *C12N 15/67* (2013.01); *C12N 2310/532* (2013.01)
(58) Field of Classification Search
  CPC .. C12N 15/11; C12N 2310/532; C12N 15/67; A61K 48/0058; G16B 30/10
  See application file for complete search history.

(56) References Cited

U.S. PATENT DOCUMENTS

| 5,773,244 A | 6/1998 | Ares et al. |
| 2020/0080106 A1 | 3/2020 | Anderson et al. |
| 2023/0279389 A1 | 9/2023 | Qiu et al. |

FOREIGN PATENT DOCUMENTS

| CN | 105985978 | 10/2016 |
| CN | 111378686 | 7/2020 |

(Continued)

OTHER PUBLICATIONS

Burke et al., "Structural conventions for group I introns," Nucleic acids research, Sep. 25, 1987, 15(18):7217-7221.

(Continued)

*Primary Examiner* — Kaijiang Zhang
(74) *Attorney, Agent, or Firm* — Fish & Richardson P.C.

(57) ABSTRACT

The present disclosure relates to a recombinant nucleic acid molecule based on point mutation of translation initiation element and use thereof in the preparation of circular RNA, and in particular to a recombinant nucleic acid molecule for preparing circular RNA, a recombinant expression vector, circular RNA, a composition, a method for preparing circular RNA, a method for expressing a target polypeptide in a cell, a method for preventing or treating a disease, a method for editing a translation initiation element sequence, and a system for editing a translation initiation element sequence. The recombinant nucleic acid molecule provided by the present disclosure provides a novel Clean PIE system for the in vitro preparation of circular RNA, which can avoid introducing additional exon sequences into circular RNA, improve sequence accuracy of circular RNA molecules, reduce changes in a secondary structure of circular RNA, and then reduce immunogenicity of circular RNA, and has a good application prospect in the fields of nucleic acid vaccines, expression of therapeutic proteins, gene therapy, etc.

14 Claims, 18 Drawing Sheets

Specification includes a Sequence Listing.

(56) References Cited

FOREIGN PATENT DOCUMENTS

| | | |
|---|---|---|
| CN | 112399860 | 2/2021 |
| CN | 112481289 | 3/2021 |
| CN | 114438127 | 5/2022 |
| CN | 114574473 A | 6/2022 |
| CN | 114574483 A | 6/2022 |
| WO | WO 2010084371 | 7/2010 |
| WO | WO 2016011222 | 1/2016 |
| WO | WO 2017/222911 | 12/2017 |
| WO | WO 2018/237372 | 12/2018 |
| WO | WO 2019236673 A1 | 12/2019 |
| WO | WO 2021189059 | 9/2021 |
| WO | WO 2022006399 A1 | 1/2022 |

OTHER PUBLICATIONS

Chen et al., "Initiation of protein synthesis by the eukaryotic translational apparatus on circular RNAs," Science, Apr. 21, 1995, 268(5209):415-417.

Djebali et al., "Landscape of transcription in human cells," Nature, Sep. 2012, 489(7414):101-108.

Gaglione et al., "Current Methods in Synthesis of Cyclic Oligonucleotides and Analogues," Current Organic Chemistry, Jun. 1, 2012, 16(11):1371-1389.

Guttman et al., "Ab initio reconstruction of cell type-specific transcriptomes in mouse reveals the conserved multi-exonic structure of lincRNAs," Nature biotechnology, May 2010, 28(5):503-510.

Jeck et al., "Detecting and characterizing circular RNAs," Nature biotechnology, May 2014, 32(5):453-461.

Kantoff et al., "Correction of adenosine deaminase deficiency in cultured human T and B cells by retrovirus-mediated gene transfer," Proceedings of the National Academy of Sciences, Sep. 1986, 83(17):6563-6567.

Kelly et al., "Exon skipping is correlated with exon circularization," Journal of molecular biology, Jul. 31, 2015, 427(15):2414-2417.

Kohn et al., "Establishment and characterization of adenosine deaminase-deficient human T cell lines," The Journal of Immunology, Jun. 1, 1989, 142 (11): 3971-3977, Abstract only.

Leppek et al., "An optimized streptavidin-binding RNA aptamer for purification of ribonucleoprotein complexes identifies novel ARE-binding proteins," Nucleic acids research, Jan. 1, 2014, 42(2):e13, 15 pages.

Liu et al., "RNA circles with minimized immunogenicity as potent PKR inhibitors," Molecular Cell, Jan. 20, 2022, 82(2): 22 pages.

Mortazavi et al., "Mapping and quantifying mammalian transcriptomes by RNA-Seq," Nature methods, Jul. 2008, 5(7):621-628.

Obi et al., "The design and synthesis of circular RNAs," Methods, Dec. 1, 2021, 196: 19 pages.

Wang et al., "Alternative isoform regulation in human tissue transcriptomes," Nature, Nov. 2008, 456(7221):470-476.

Wang et al., "Efficient backsplicing produces translatable circular mRNAs," Rna, Feb. 1, 2015, 21(2): 8 pages.

Wilusz et al., "Long noncoding RNAs: functional surprises from the RNA world," Genes & development, Jul. 1, 2009, 23(13):1494-1504.

Wilusz, "A 360 view of circular RNAs: From biogenesis to functions," Wiley Interdisciplinary Reviews: RNA, Jul. 2018, 9(4):e1478, 17 pages.

Rausch et al., "Characterizing and circumventing sequence restrictions for synthesis of circular RNA in vitro," Nucleic Acids Research, Apr. 6, 2021, 49(6):e35, 13 pages.

Chen et al., "Sensing self and foreign circular RNAs by intron identity," Molecular Cell, Jul. 20, 2017, 67(2):228-38.

Wesselhoeft et al., "Engineering circular RNA for potent and stable translation in eukaryotic cells," Nature Communications, Jul. 6, 2018, 9(1):2629, 10 pages.

Chen et al., "Study of circular RNA translation using reporter systems in living cells," Methods, Dec. 2021, 196:113-20.

Costello et al., "Reinventing the wheel: synthetic circular RNAs for mammalian cell engineering," Trends in Biotechnology, Feb. 2020, 38(2):217-30.

Liu et al., "RNA circles with minimized immunogenicity as potent PKR inhibitors," Molecular Cell, Jan. 2022, 82(2):420-34.

Qiu et al., Clean-PIE: a novel strategy for efficiently constructing precise circRNA with thoroughly minimized immunogenicity to direct potent and durable protein expression, bioRxiv, Jun. 2022, Jun. 2022.

Qu et al., "Circular RNA vaccines against SARS-COV-2 and emerging variants," Cell, May 2022, 185(10):1728-44.

Chen et al., "Circular RNA: Biosynthesis in vitro," Frontiers in Bioengineering and Biotechnology, Nov. 30, 2021, 9:787881, 11 pages.

Li, "CircIRAK3 sponges miR-3607 to facilitate breast cancer metastasis," Master's thesis of Nanjing Medical University, May 2019, 86 pages (with English abstract).

Li, "The protective role and mechanisms of circRNAs in BPA induced spermatocyte toxicity," Huazhong University of Science & Technology, 221 pages (with English abstract), May 2019.

Qiu et al., "Clean-PIE: a novel strategy for efficiently constructing precise circRNA with thoroughly minimized immunogenicity to direct potent and durable protein expression," bioRxiv, Jun. 2022, 30 pages.

EP Extended European Search Report in European Appln. No. 22186592.6, mailed on Jul. 13, 2023, 8 pages.

Petkovic et al., "RNA circularization strategies in vivo and in vitro," Nucleic Acids Research, Feb. 2015, 43(4):2454-65.

Prats et al., "Circular RNA, the key for translation," International Journal of Molecular Sciences, Nov. 2020, 21(22):8591.

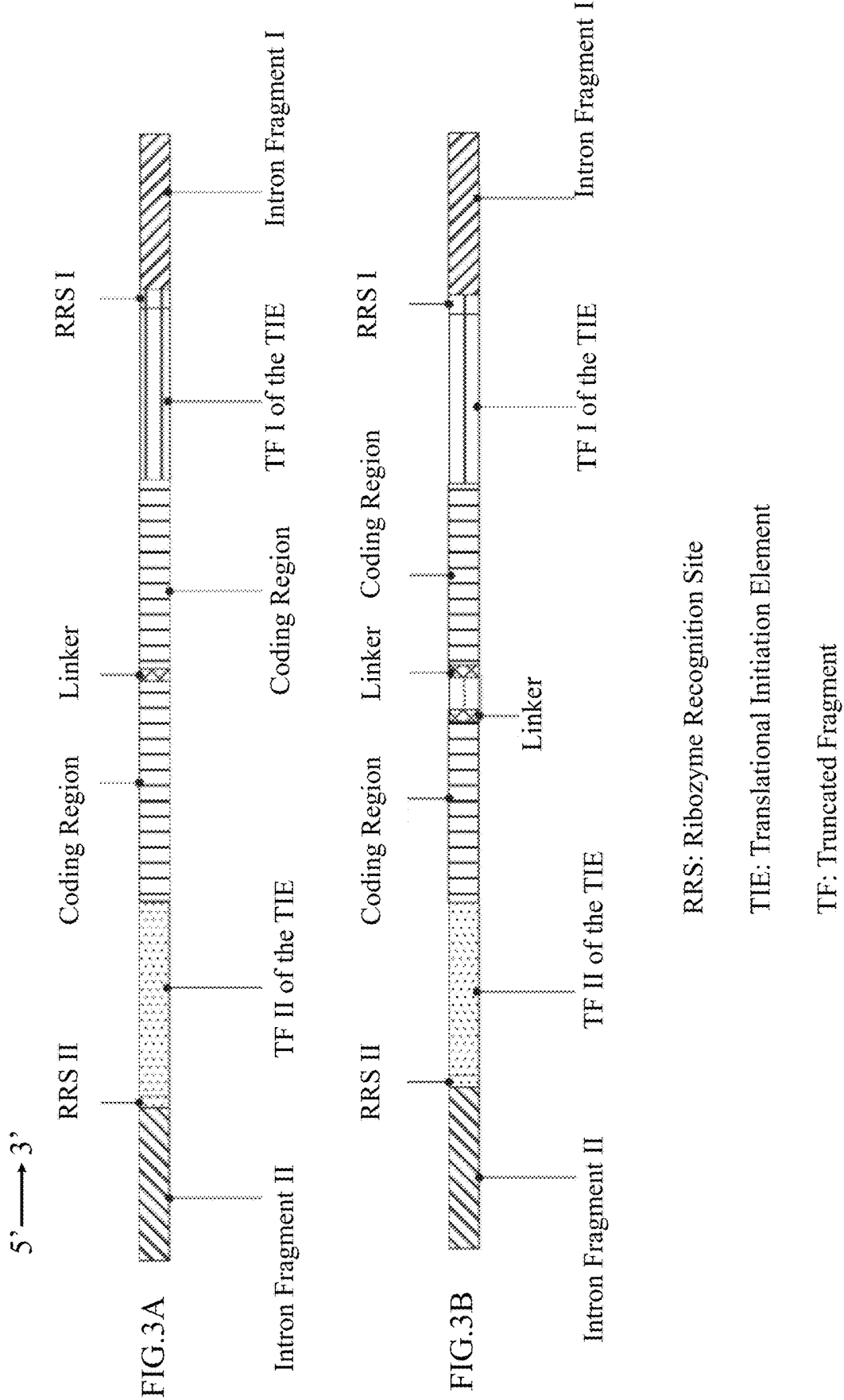

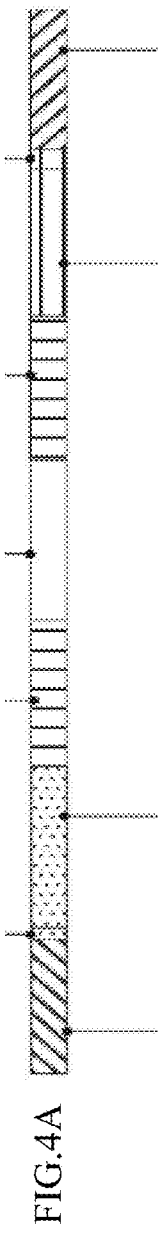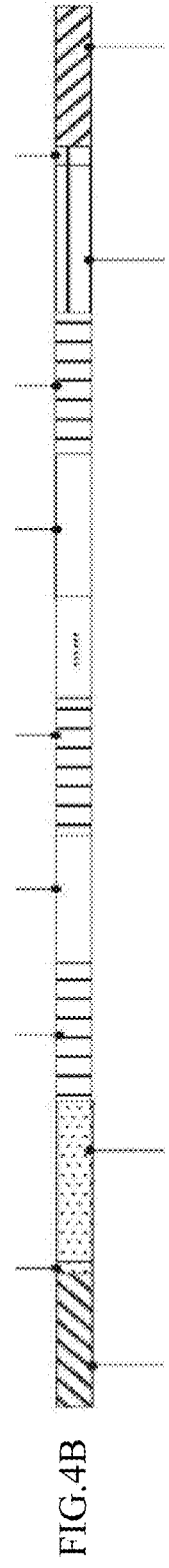
FIG. 4A
FIG. 4B
RRS: Ribozyme Recognition Site
TIE: Translational Initiation Element
TF: Truncated Fragment

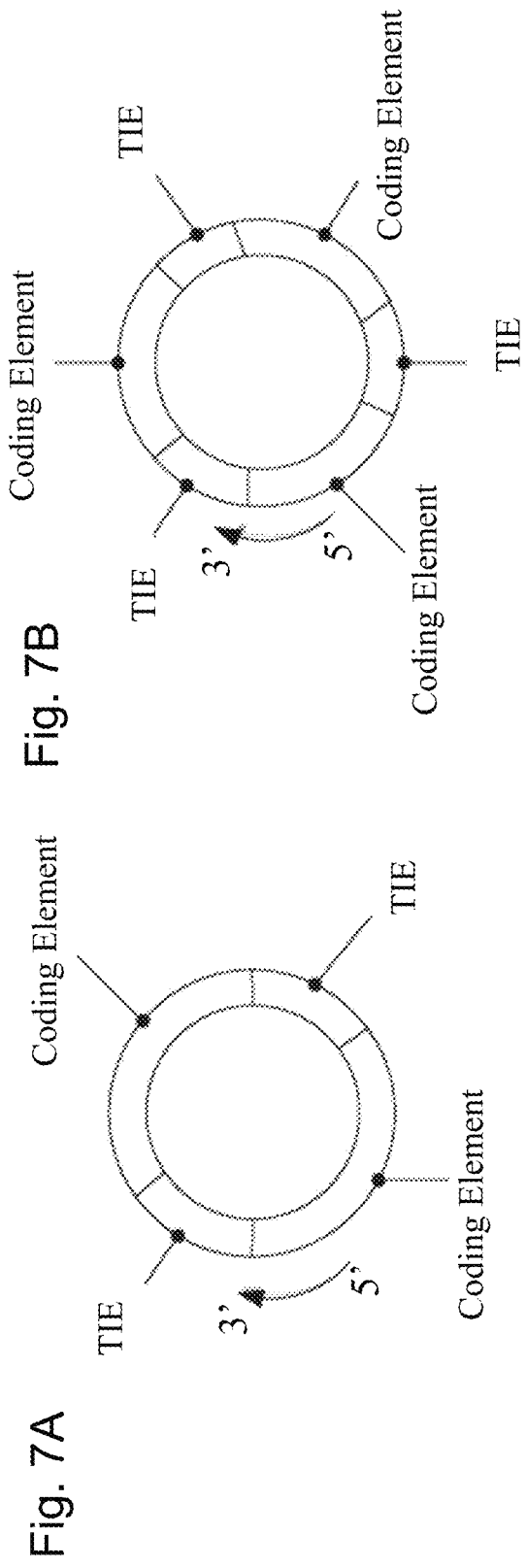

RECOMBINANT NUCLEIC ACID MOLECULE BASED ON POINT MUTATION OF TRANSLATION INITIATION ELEMENT AND USE THEREOF IN PREPARATION OF CIRCULAR RNA

CROSS-REFERENCE TO RELATED APPLICATIONS

The present application claims the benefits and priority to the Chinese Patent Application No. 202210200186.X filed with the National Intellectual Property Administration, PRC on Mar. 2, 2022, the content of which is incorporated herein by reference in its entirety.

TECHNICAL FIELD

The present disclosure belongs to the fields of molecular biology and bioengineering technology, and in particular, the present disclosure relates to a recombinant nucleic acid molecule for preparing circular RNA, a recombinant expression vector, a circular RNA, a composition, a method for preparing circular RNA, a method for expressing a target polypeptide in a cell, a method for preventing or treating a disease, a method for editing a translation initiation element sequence, and a system for editing a translation initiation element sequence.

BACKGROUND

Messenger ribonucleic acid (mRNA) is transcribed from DNA and provides necessary genetic information for the next step of protein translation. It has important application value in protein production, gene therapy approaches such as using as nucleic acid vaccines, and the like. Compared with traditional vaccines, nucleic acid vaccines have various advantages, such as long-lasting immune response, simple manufacturing process, and applications in tumor prevention, and have broad prospects in the fields of acute infectious diseases, HIV and cancer prevention and the like. In particular, since the outbreak of the novel Corona Virus Disease 2019 (COVID-19), the research and development of nucleic acid vaccines has been significantly accelerated. Although circular RNAs (circRNAs) mediated by internal ribosome entry sites (IRES) have been shown to synthesize proteins in vitro in a cap-independent manner, for a long time in the past, most researchers still believed that eukaryotic ribosomes could not translate circRNAs in vivo. With the emergence of RNA sequencing (RNA-seq) technology, more and more circRNAs have been identified, and the research of circRNAs has been paid more attention. Along with the deepening of research, researchers found that circRNAs not only exist widely in eukaryotes, but also are highly conserved. CircRNA exhibits higher resistance to RNase than linear mRNA since its 5' and 3' ends are ligated end-to-end to form a closed loop; therefore enabling the circRNA longer-acting and lasting expression compared with linear mRNA. In addition, the production of circRNA is more efficient, faster, and less expensive, compared with cumbersome capping, tailing and nucleotide modification in the production of linear mRNA. Due to these properties, although circRNA is a bran-new gene therapy approach, it has been commercially developed as a vector for gene therapy.

Circularization of RNA is a key step in the production and processing of circRNA. At present, the common methods for circularization are mainly divided into in vivo circularization and in vitro circularization. In eukaryotes, spliceosome cleaves an intron from immature mRNA in two steps. The details are as follows: first, 2'-hydroxyl on a specific branch point Adenosine (bpA) in the intron attacks a splicing site at the 5' end, thereby forming a 3'-hydroxyl at an exon end at the 5' end; and then, the newly formed 3'-hydroxyl end further attacks a splicing site at the 3' end with the aid of the spliceosome to form a linear RNA ligated to two exons and a lariat. Natural circRNAs are generated in this process by back-splicing or exon skipping. Although the in vivo circularization process can ensure the accuracy of the circRNA sequence after circularization, a plasmid needs to be introduced into the body as a therapeutic agent, which greatly increases the risk of integration into the genome. The in vitro circularization of RNA mainly depends on the formation of a phosphodiester bond, and the most common in vitro circularization of RNA is mainly divided into chemical circularization method and enzymatic circularization method. Among them, a natural phosphodiester bond in the chemical circularization method is mainly formed by condensation reaction of RNA 5'-monophosphate and 3'-hydroxyl catalyzed by cyanogen bromide or ethyl-3-(3'-dimethylaminopropyl)-carbodiimide. However, the chemical circularization method has low ligation efficiency, and is only suitable for ligation of small fragments of circRNA. Moreover, chemical groups also have great safety risks during gene therapy. Therefore, chemical circularization method is difficult to be widely used. The enzymatic circularization method can be further divided into protease-catalyed circularization and ribozyme-catalyed circularization, wherein the formation of a phosphodiester bond in the protease-catalyed circularization is mainly catalyzed by T4 DNA ligase, T4 RNA ligase 1, T4 RNA ligase 2 and RtcB through a splint chain. However, current methods of protease-catalyzed ligation have low ligation efficiency in large fragments of circRNAs and difficulty of obtaining circular messenger ribonucleotides with accurate nucleic acid sequences. Ribozyme is a type of RNA that acts as a catalyst similar to protease. There are generally three methods for in vitro production of circRNA by ribozyme, i.e., Group I intron self-splicing, Group II intron self-splicing and circularization through some subviral genomes. Among them, Group II intron is usually ligated into a loop through 2',5'-diphosphate. Whether such ligation affects the expression of circRNA needs further investigation. The way of forming circRNA through a subviral genome usually requires the introduction of ribozymes of the subviral genome, and some RNAs in the body usually become potential targets for cleavage by these ribozymes. Circularization of circular ribonucleotides catalyzed by Group I intron is currently a common circularization strategy in the industry, in which *Anabaena* premuted intron exon (PIE) and thymidylate synthase of T4 (T4td) PIE are currently the most widely used ribozyme-catalyzed self-cleaving circularization systems. In the presence of guanine and divalent cations, the intron sequences of *Anabaena* PIE and T4td PIE form specific structures and are cut down by self-catalysis, thereby circularizing the ribonucleotide sequence in the middle of the intron.

Chinese patent document CN 112399860 A discloses a vector for preparing circRNA, the vector including the following elements operably ligated to each other and arranged in the following order: a.) a 5' homologous arm, b.) a 3' Group I intron fragment including a 3' splicing site dinucleotide, c.) optionally, a 5' spacer sequence, d.) a protein coding or non-coding region, e.) optionally, a 3' spacer sequence, f.) a 5' Group I intron fragment including a 5' splicing site dinucleotide, and g.) a 3' homologous arm, and the vector allowing the production of a translatable or biologically active circRNAs in eukaryotic cells. Although the vector can be used to prepare circRNA through the self-splicing property of a PIE system, a specific exon sequence needs to be inserted into the vector to guide splicing of the intron fragment, and an additional exon sequence will be introduced into the finally obtained circRNA, which reduces the sequence accuracy of the circRNA, resulting in great changes in the structure and conformation of RNA after circularization, triggering cellular immune responses, inducing degradation of the circRNA in cells, making the circRNA a potential safety hazard in nucleic acid vaccines and in gene therapy, and limiting the application of circRNA in clinical disease treatment.

SEQUENCE LISTING

This application contains a Sequence Listing that has been submitted electronically as an XML file named "53596-0005004001.XML" The XML file, created Jul. 19, 2022 is 54,090 bytes in size. The material in the XML file is hereby incorporated by reference in its entirety.

SUMMARY

Problems to be Solved by the Invention

In view of the problems existing in the prior art, e.g., the current method for preparing circRNA in vitro using a PIE system results in the inclusion of additional exon sequences in the circRNA, leading to changes in the structure and conformation of the circRNA, and triggering cellular immune responses, and the circRNA molecules are susceptible to degradation in vivo and have potential safety hazards in terms of nucleic acid vaccines, gene therapy and the like. To this end, the present disclosure provides a recombinant nucleic acid molecule that can be used for the in vitro preparation of circRNA; furthermore, the circRNA prepared by using the recombinant nucleic acid molecule can avoid introduction of additional exon sequences, improve sequence accuracy of circRNA molecules, reduce changes in a secondary structure of circRNA, and then reduce immunogenicity of circRNA, improve intracellular stability of circRNA, and reduce safety risk of circRNA in clinical application, and has broad application prospects in the fields of mRNA infectious disease vaccines, therapeutic mRNA tumor vaccines, mRNA-based dendritic cell (DC) tumor vaccines, mRNA-based gene therapy and protein supplement therapy, etc.

Solutions to the Problems (1) A recombinant nucleic acid molecule for preparing a circular RNA, wherein in the 5' to 3' direction, the recombinant nucleic acid molecule includes elements arranged in the following order:
intron fragment II, truncated fragment II of the translational initiation element, a coding element encoding at least one target polypeptide, truncated fragment I of the translation initiation element, and intron fragment I;
wherein the 3' end of the truncated fragment I of the translation initiation element includes ribozyme recognition site I consisting of a first predetermined number of nucleotides located at the 3' end of the truncated fragment I of the translation initiation element;

the 5' end of the truncated fragment II of the translational initiation element includes ribozyme recognition site II consisting of a second predetermined number of nucleotides located at the 5' end of the truncated fragment II of the translational initiation element;
the nucleotide sequence of the truncated fragment I of the translation initiation element and the nucleotide sequence of the truncated fragment II of the translational initiation element are used to form a translation initiation element sequence in the 5' to 3' direction; the nucleotide sequence of the truncated fragment I of the translation initiation element corresponds to a partial sequence of the translation initiation element sequence near the 5' direction, and the nucleotide sequence of the truncated fragment II of the translational initiation element corresponds to the remaining partial sequence of translation initiation element sequence near the 3' direction;
the nucleotide sequence of the intron fragment I and the nucleotide sequence of the intron fragment II are used to form an intron sequence in the 5' to 3' direction; the nucleotide sequence of intron fragment I includes a partial sequence of the intron sequence near the 5' direction, and the nucleotide sequence of intron fragment II includes the remaining partial sequence of the intron sequence near the 3' direction.

(2) The recombinant nucleic acid molecule according to (1), wherein the intron fragment I and the intron fragment II are derived from Group I intron, the ribozyme recognition site I is derived from a natural exon sequence ligated to the 5' end of the intron fragment I, and the ribozyme recognition site II is derived from a natural exon sequence ligated to the 3' end of the intron fragment II; and
optionally, the Group I intron is derived from any one of the following Group I introns: T4 phage td gene, *Anabaena* tRNA$^{Leu}$, TpaCOX2, and Ptu.

(3) The recombinant nucleic acid molecule according to (1) or (2), wherein the first predetermined number of nucleotides is selected from 3 to 100 nucleotides, preferably 3 to 50 nucleotides, and more preferably 3 to 10 nucleotides.

(4) The recombinant nucleic acid molecule according to any one of (1) to (3), wherein the second predetermined number of nucleotides is selected from 1 to 100 nucleotides, preferably 1 to 50 nucleotides, and more preferably 1 to 10 nucleotides.

(5) The recombinant nucleic acid molecule of any one of (1) to (4), wherein the sum of the first predetermined number and the second predetermined number is not equal to 3y, y≥1 and y is an integer.

(6) The recombinant nucleic acid molecule according to any one of (1) to (5), wherein the translation initiation element sequence is a sequence having an activity of initiating translation of the coding element; and
optionally, the translation initiation element sequence includes one or a combination of two or more of the following sequences: an IRES sequence, a 5'UTR sequence, a Kozak sequence, a sequence with m$^6$A modification, and a complementary sequence of ribosomal 18S rRNA.

(7) The recombinant nucleic acid molecule of any one of (1) to (6), wherein the coding element includes at least one coding region; and optionally, the coding element includes at least two coding regions, and each coding region independently encodes any type of target polypeptide.

(8) The recombinant nucleic acid molecule according to (7), the coding element including at least two coding regions, wherein a linker is linked between any two adjacent coding regions; and preferably, the linker is a polynucleotide encoding a 2A peptide.

(9) The recombinant nucleic acid molecule according to (7), the coding element comprising at least two coding regions, wherein a translation initiation element is ligated between any two adjacent coding regions; and optionally, the translation initiation element located between any two adjacent coding regions includes one or a combination of two or more of the following sequences: an IRES sequence, a 5'UTR sequence, a Kozak sequence, a sequence with $m^6A$ modification, and a complementary sequence of ribosomal 18S rRNA.

(10) The recombinant nucleic acid molecule according to any one of (1) to (9), wherein the target polypeptide is a human-derived protein or a non-human-derived protein; and optionally, the target polypeptide is selected from one or a combination of two or more of the following: an antigen, an antibody, an antigen-binding fragment, a fluorescent protein, a protein with therapeutic activity against a disease, and a protein with gene editing activity.

(11) The recombinant nucleic acid molecule according to any one of (1) to (10), wherein the recombinant nucleic acid molecule further comprises an insertion element between the coding element and the truncated fragment I of the translation initiation element;

the insertion element is at least one selected from the group consisting of (i) to (iii):

(i) a transcriptional level regulatory element, (ii) a translational level regulatory element, and (iii) a purification element;

optionally, the insertion element includes a sequence of one or a combination of two or more of the following: an untranslated region sequence, a polyA sequence, an aptamer sequence, a riboswitch sequence, and a sequence that binds to a transcriptional regulator.

(12) The recombinant nucleic acid molecule according to any one of (1) to (11), wherein the recombinant nucleic acid molecule further comprises a 5' homologous arm and a 3' homologous arm, and the nucleotide sequence of the 5' homologous arm hybridizes to the nucleotide sequence of the 3' homologous arm;

the 5' homologous arm is ligated to the 5' end of the intron fragment II, and the 3' homologous arm is ligated to the 3' end of the intron fragment I.

(13) The recombinant nucleic acid molecule according to any one of (1) to (12), wherein an interior of any one of the intron fragment I, the coding element and the intron fragment II does not include a nucleotide sequence derived from an exon; alternatively, an exon-derived nucleotide sequence is not included between any two of the intron fragment I, the truncated fragment II of the translational initiation element, the coding element, the translation initiation element truncation fragment I and the intron fragment II.

(14) A recombinant expression vector, wherein the recombinant expression vector comprises the recombinant nucleic acid molecule according to any one of (1) to (13).

(15) Use of the recombinant nucleic acid molecule according to any one of (1) to (13), or the recombinant expression vector according to (14), for the preparation of circular RNA in vitro.

(16) A method for preparing circular RNA in vitro, comprising the following steps:

transcription step: transcribing the recombinant nucleic acid molecule according to any one of (1) to (13) or the recombinant expression vector according to (14) to form a circularized precursor nucleic acid molecule;

circularization step: subjecting the circularized precursor nucleic acid to a circularization reaction to obtain circular RNA; and optionally, the method further comprises a step of purifying the circular RNA.

(17) A circular RNA prepared by the recombinant nucleic acid molecule according to any one of (1) to (13), the recombinant expression vector according to (14), or the method according to (16).

(18) A circular RNA comprising, in the 5' to 3' direction, elements arranged in the following order:

a translation initiation element, a coding element encoding at least one target polypeptide;

optionally, the circRNA includes an insertion element between the 5' end of the translation initiation element and the 3' end of the coding element;

optionally, the translation initiation element, the target polypeptide or the insertion element are as defined according to any one of (6) and (10) to (11).

(19) The circular RNA according to (18), wherein the coding element of the circular RNA comprises at least two coding regions, each coding region independently encodes any type of target polypeptide; wherein a linker is linked between any two adjacent coding regions;

preferably, the linker is a polynucleotide encoding a 2A peptide.

(20) The circular RNA according to (18), wherein the coding element of the circular RNA comprises at least two coding regions, each coding region independently encodes any type of target polypeptide; wherein a translation initiation element is ligated between any two adjacent coding regions;

optionally, the translation initiation element located between any two adjacent coding regions includes one or a combination of two or more of the following sequences: an IRES sequence, a 5'UTR sequence, a Kozak sequence, a sequence with $m^6A$ modification, and a complementary sequence of ribosomal 18S rRNA.

(21) A composition comprising the recombinant nucleic acid molecule according to any one of (1) to (13), the recombinant expression vector according to (14), or the circular RNA according to any one of (17) to (20); preferably comprising the circular RNA as defined in any one of (17) to (20), optionally, the composition further includes one or two or more pharmaceutically acceptable carriers;

optionally, the pharmaceutically acceptable carrier is selected from a lipid, a polymer or a lipid-polymer complex.

(22) A method for expressing a target polypeptide in a cell, wherein the method comprises a step of transferring the circular RNA according to any one of (17) to (20), or the composition according to (18), into a cell.

(23) A method for preventing or treating a disease, wherein the method comprises administering to a subject the circular RNA according to any one of (17) to (20), or the composition according to (21).

(24) A method for editing a translation initiation element sequence, wherein the method comprises the following steps:
  S1, determining a secondary structure of the translation initiation element according to the translation initiation element sequence;
  S2, determining a to-be-edited region in the translation initiation element sequence according to the secondary structure; and
  S3, substituting base(s) at any one or two or more positions in the to-be-edited region to obtain an editing region including a ribozyme recognition site.

(25) The method according to (24), wherein a sequence of the ribozyme recognition site is formed by ligating the nucleotide sequence of ribozyme recognition site I with the nucleotide sequence of ribozyme recognition site II.

(26) The method according to (24) or (25), wherein the no hairpin structure of more than 20 bp is presented within the range of 100 bp upstream and 100 bp downstream of the to-be-edited region.

(27) A system for editing a translation initiation element sequence, wherein the system comprises:
  a secondary structure constructing module used for determining a secondary structure of the translation initiation element according to the translation initiation element sequence;
  a to-be-edited region screening module used for determining a to-be-edited region in the translation initiation element sequence according to the secondary structure; and
  a base substitution module used for substituting base(s) at any one or two or more positions in the to-be-edited region to obtain an editing region including a ribozyme recognition site.

(28) The system according to (27), wherein a sequence of the ribozyme recognition site is formed by ligating the nucleotide sequence of ribozyme recognition site I with the nucleotide sequence of ribozyme recognition site II.

(29) The system according to (27) or (28), wherein no hairpin structure of more than 20 bp is presented within the range of 100 bp upstream and 100 bp downstream of the to-be-edited region.

Effects of the Invention

In some embodiments, the recombinant nucleic acid molecule for preparing circRNA provided by the present invention includes intron fragment II, truncated fragment II of the translational initiation element, a coding element encoding at least one target polypeptide, truncated fragment I of the translation initiation element, and intron fragment I. The recombinant nucleic acid molecule can be used for preparing circRNA in vitro, and under the guidance of an intron sequence, a splicing site located at the 3' end of the truncated fragment I of the translation initiation element and a splicing site located at the 5' end of the truncated fragment II of the translational initiation element successively break, causing linear nucleic acid molecules to be ligated to form circRNA, and the truncated fragment I of the translation initiation element and the truncated fragment II of the translational initiation element are ligated to form a translation initiation element for initiating translation of the coding element. Furthermore, since the ribozyme recognition site I and the ribozyme recognition site II are formed inside the translation initiation element truncated fragments, no additional exon sequences need to be introduced into the recombinant nucleic acid molecule, thereby excluding additional exon sequences from circRNA and improving sequence accuracy of circRNA molecules.

The recombinant nucleic acid molecule of the present disclosure provides a structurally novel Clean PIE system for in vitro preparation of circRNA by introducing a ribozyme recognition site inside a translation initiation element. Compared with a classic PIE system, the Clean PIE system of the present disclosure can improve sequence accuracy of circRNA, reduce changes in a secondary structure of circRNA, thereby reducing immunogenicity of circRNA, improving intracellular stability of circRNA, and reducing safety risks of circRNA in clinical application, is suitable for large-scale production of circRNA in vitro, and has broad application prospects in the fields of mRNA infectious disease vaccines, therapeutic mRNA tumor vaccines, mRNA-based dendritic cell (DC) tumor vaccines, mRNA-based gene therapy and protein supplement therapy, etc.

In some embodiments, for the recombinant nucleic acid molecule for preparing circRNA provided by the present disclosure, there is no need to introduce fragments such as spacers, homologous arms, exons, etc. The recombinant nucleic acid molecule has a simple structure, the prepared circRNA has good safety, and is suitable for large-scale industrial preparation of circRNA in vitro.

In some embodiments, for the recombinant nucleic acid molecule for preparing circRNA provided by the present disclosure, the translation initiation element has various sequence selections, all of which enable efficient translation of coding elements in circRNA and provide various sequence selections for the production of circRNA.

In some embodiments, for the recombinant nucleic acid molecule for preparing circRNA provided by the present disclosure, by introducing the insertion element, different functional types of insertion elements, such as a transcription level regulatory element, a translation level regulatory element or a purification element, can be further introduced into circRNA, so as to achieve specific regulation on the expression of a target polypeptide by circRNA, and in vitro purification of circRNA can specifically regulate expression abundance of the target polypeptide, thereby improving therapeutic effects of circRNA on diseases.

In some embodiments, the circRNA provided by the present disclosure, prepared by using the above recombinant nucleic acid molecule, does not contain an additionally introduced exon sequence, has high sequence accuracy, little change in secondary structure, high biological safety and structural stability, and low immunogenicity, and is suitable for the field of clinical disease treatment.

In some embodiments, according to the method for editing a translation initiation element sequence provided by the present disclosure, a target coding sequence including a ribozyme recognition site can be obtained by substituting one or more bases in the translation initiation element sequence. The truncated fragment I of the translation initiation element and the truncated fragment II of the translational initiation element can be obtained by truncating a translation initiation element sequence including ribozyme recognition sites at the position of the ribozyme recognition sites; and the ribozyme recognition sites are built into the translation initiation element truncated fragments described above, avoiding the introduction of additional exon sequences into circRNA. The editing method of the present disclosure is suitable for fusing ribozyme recognition sites in any type of PIE system into the translation initiation element sequence, and has broad application prospects.

Further, the present disclosure provides a method for inserting a ribozyme recognition site by point mutation in a to-be-edited region, which has advantages of editing freedom, high sequence accuracy of the inserted ribozyme recognition site, and allowing insertion of multiple ribozyme recognition sites, and improves operability of constructing a clean PIE system.

BRIEF DESCRIPTION OF THE DRAWINGS

FIGS. 3A and 3B show a structural schematic diagram of a recombinant nucleic acid molecule (Clean PIE system) for preparation of circRNA of the present disclosure;

FIGS. 4A and 4B shows a structural schematic diagram of a recombinant nucleic acid molecule (Clean PIE system) for preparation of circRNA of the present disclosure;

FIGS. 7A and 7B shows a circRNA structure prepared using the Clean PIE system of the present disclosure;

DETAILED DESCRIPTION

Definitions

When used in conjunction with the terms "including", "comprising" or "containing" in the claims and/or the specification, the words "a" or "an" may refer to "one", but may also refer to "one or more", "at least one", and "one or more than one".

As used in the claims and specification, the words "comprising", "having", "including", or "containing" are intended to be inclusive or open-ended and do not exclude additional, unrecited elements or method steps.

Throughout this application, the term "about" means that: a value includes the standard deviation of error for the device or method being employed to determine the value.

Although the disclosure supports the definition of the term "or" as a mere alternative and "and/or", the term "or" in the claims means "and/or" unless explicitly indicated to be a mere alternative or mutually exclusive.

The terms "polypeptide", "peptide" and "protein" are used interchangeably herein and are amino acid polymers of any length. The polymers may be linear or branched, may contain modified amino acids, and may be interrupted by non-amino acids. The term also includes amino acid polymers that have been modified (e.g., disulfide bond formation, glycosylation, lipidation, acetylation, phosphorylation, or any other manipulation, such as conjugation with a labeling component).

As used in the present disclosure, the "PIE system", also known as permuted introns and exons, is a process of ligating to form circRNA using a self-splicing system of Group I introns.

As used in the present disclosure, Group I intron has a self-splicing system for circularization in the presence of GTP and $Mg^{2+}$.

Figure 14:
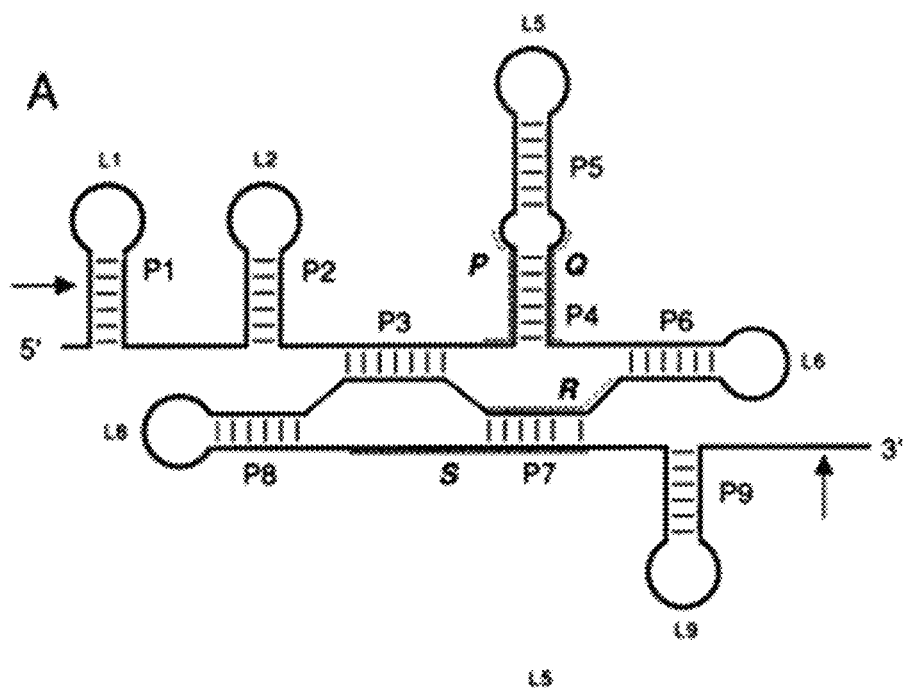
FIG. 14 shows structural features of Group I intron.

The group I intron is a class of super large ribozymes that can undergo self-splicing reactions, which is commonly found in many species, and is mainly involved in the catalytic cleavage of precursors of mRNA, tRNA and rRNA. Its core secondary structure typically includes nine pairing regions (P1-P9) and corresponding loop regions (L1-L9) (FIG. 14). Splicing of Group I intron is performed through two consecutive transesterification reactions. Exogenous guanosine or guanosine nucleotide (G) first docks at an active G binding site at P7 with its 3'-OH aligned to attack the phosphodiester bond at the 5' splicing site of Pl, resulting in a free 3'-OH group at the upstream exon with the exogenous G linked to the 5' end of the intron. The terminal G (omega G) of the intron is then exchanged for a exogenous G, occupying the G binding site, and organizing a second transesterification reaction: the 3'-OH group of the P1 upstream exon aligns to attack the 3' splicing P10 site, resulting in the ligation of adjacent upstream and downstream exons and release of a catalytic intron. The Group I intron generally includes structural features as shown in FIG. 14 (derived from Burke J M, belfort M, cech T R, et al. Structural conventions for group I introns [J]. Nucleic acids research, 1987, 15(18): 7217-7221).

As used in the present disclosure, an internal guide sequence generally refers to a nucleotide sequence in Group I intron that is paired with a corresponding exon sequence by either a Watson-Crick pairing or a wobble pairing, typically in P1 stem in Group I intron.

As used in the present disclosure, "ribozyme" is used to describe RNA that has catalytic activity. In some embodiments, a ribozyme recognition site in the present disclosure refers to a polynucleotide sequence capable of being recognized by a ribozyme and having an internal phosphodiester bond breaking, when RNA forms a ribozyme molecule with catalytic function.

As used in the present disclosure, the term "circular nucleic acid molecule" refers to a nucleic acid molecule in a closed loop form. In some specific embodiments, the circular nucleic acid molecule is a circular RNA molecule. More specifically, the circular nucleic acid molecule is a circular mRNA molecule.

As used in the present disclosure, the term "linear RNA" refers to a circRNA precursor capable of forming a circRNA through a circularization reaction, which is typically formed by transcription from a linear DNA molecule (e.g., a vector containing a recombinant nucleic acid molecule, etc.).

As used in the present disclosure, the term "IRES" is also referred to as an internal ribosome entry site. An "internal ribosome entry site" (IRES) belongs to a translation control sequence, usually located at the 5' end of a gene of interest, and allows translation of RNA in a cap-independent manner. The transcribed IRES can bind directly to a ribosomal subunit such that a mRNA initiation codon is properly oriented in the ribosome for translation. The IRES sequence is usually located in the 5'UTR of mRNA (directly upstream of the initiation codon). IRES functionally replaces the need for a variety of protein factors that interact with eukaryotic translation mechanisms.

As used in the present disclosure, the term "translation initiation element" refers to any sequence element capable of recruiting ribosomes, initiating a translation process of an RNA molecule. Illustratively, the translation initiation element is an IRES element, a sequence with $m^6A$ modification, or an initiation sequence for rolling circle translation, and the like.

The term "coding region" refers to a gene sequence capable of transcribing messenger RNA and finally translating it into a target polypeptide, or protein.

The term "expression" includes any step involving the production of a polypeptide, including, but not limited to: transcription, post-transcriptional modification, translation, post-translational modification, and secretion.

The term "antibody" is used herein in the broadest sense, refers to a protein including an antigen-binding site and encompasses natural and artificial antibodies of various structures including, but not limited to, polyclonal, monoclonal, monospecific, multispecific, nonspecific, humanized, single-chain, chimeric, synthetic, recombinant, hybrid, mutant, and grafted antibodies. The term "antibody" also includes antibody fragments such as Fab, F (ab')$_2$, FV, scFv, Fd, dAb and other antibody fragments that retain the antigen binding function. Typically, such fragments will include antigen-binding fragments.

As used in the present disclosure, the term "hybridization" refers to a process by which a base on one nucleic acid strand binds to a complementary base on the other nucleic acid strand through base pairing. Hybridization reactions can be selective, such that a particular sequence of interest can be selected from a sample when it is present at low concentrations. Stringency of hybridization conditions (e.g., high stringency, medium stringency, stringency) can be adjusted by, for example, concentrations of salt or formamide in a prehybridization solution and a hybridization solution, or hybridization temperature. For example, the stringency can be increased by decreasing the salt concentration, increasing the formamide concentration, or increasing the hybridization temperature. Generally, stringent conditions include hybridization at a temperature of about 25° C. to about 42° C. in at least about 0% to at least about 15% v/v formamide and at least about 1 M to at least about 2 M salt, and washing in at least about 1 M to at least about 2 M salt; moderately stringent conditions include hybridization at a temperature of about 25° C. to about 65° C. in at least about 16% to at least about 30% v/v formamide and at least about 0.5 M to at least about 0.9 M salt, and washing in at least about 0.5 M to at least about 0.9 M salt; and highly stringent conditions include hybridization at a temperature of about at least 65° C. in at least about 31% to at least about 50% v/v formamide and at least about 0.01 M to at least about 0.15 M salt, and washing in at least about 0.01 M to at least about 0.15 M salt; formamide is optional in these hybridization conditions. Other suitable hybridization buffers and conditions are well known to those skilled in the art and are described, for example, in Sambrook et al. Molecular Cloning: A Laboratory Manual, 2nd ed. Cold Spring Harbor Press, plainview, N.Y. (1989); and Ausubel et al. Short Protocols in Molecular Biology, 4 th ed. John Wiley & Sons (1999).

The term "pharmaceutically acceptable carrier" used in the context of the present disclosure refers to auxiliary materials that are widely used in the field of pharmaceutical manufacture. The primary purpose of using the carrier is to provide a pharmaceutical composition that is safe for use and stable in properties, and/or has specific functionality, and also to provide a method for dissolution of an active ingredient at a desired rate after administration of a drug to a subject, or to facilitate effective absorption of the active ingredient in the subject receiving administration. The pharmaceutically acceptable carrier can be an inert filler or a functional ingredient that provides some function to the pharmaceutical composition, such as stabilizing the overall pH of the composition or preventing degradation of the active ingredient in the composition. Non-limiting examples of the pharmaceutically acceptable carrier include, but are not limited to, binders, suspending agents, emulsifiers, diluents (or fillers), granulating agents, adhesives, disintegrants, lubricants, anti-adherents, glidants, wetting agents, gelling agents, absorption delaying agents, dissolution inhibitors, enhancers, adsorbents, buffers, chelating agents, preservatives, colorants, flavors, sweeteners, and the like.

As used in the present disclosure, the terms "complementary" or "hybridized" are used to refer to "polynucleotides" and "oligonucleotides" (which are interchangeable terms and refer to nucleotide sequences) in relation to base-pairing rules. For example, the sequence "CAGT" is complementary to the sequence "GTCA". Complementation or hybridization may be "partial" or "complete". "Partial" complementation or hybridization means that one or more nucleic acid bases are mismatched according to the base pairing rules, and "total" or "complete" complementation or hybridization between nucleic acids means that each nucleic acid base matches with the other base under the base pairing rules. Degree of complementation or hybridization between nucleic acid strands has a significant effect on efficiency and strength of hybridization between nucleic acid strands. This is particularly important in amplification reactions and detection methods that depend on binding between nucleic acids.

The term "recombinant nucleic acid molecule" refers to a polynucleotide having sequences that are not linked together in nature. The recombinant polynucleotide may be included in a suitable vector, and the vector may be used for transformation into a suitable host cell. The polynucleotide is then expressed in a recombinant host cell to produce, for example, a "recombinant polypeptide", a "recombinant protein", and a "fusion protein".

The term "recombinant expression vector" refers to a DNA structure used to express, for example, a polynucleotide encoding a desired polypeptide. A recombinant expression vector may include, for example, i) a collection of genetic elements having a regulatory effect on gene expression, such as promoters and enhancers; ii) a structure or coding sequence that is transcribed into mRNA and translated into a protein; and iii) appropriate transcriptional subunits of transcription and translation initiation and termination sequences. Recombinant expression vectors can be constructed in any suitable manner. The nature of the vector is not critical and any vector may be used, including plasmids, viruses, phages and transposons. Possible vectors for use in the present disclosure include, but are not limited to, chromosomal, non-chromosomal and synthetic DNA sequences, such as viral plasmids, bacterial plasmids, phage DNA, yeast plasmids and vectors derived from combinations of plasmids and phage DNA, and DNA from viruses such as lentiviruses, retroviruses, vaccinia, adenoviruses, fowlpox, baculoviruses, SV40, and pseudorabies.

The term "host cell" refers to a cell into which an exogenous polynucleotide has been introduced, and includes the progeny of such a cell. Host cells include "transformants" and "transformed cells", which include primary transformed cells and progeny derived therefrom. Host cells are any type of cellular system that can be used to produce antibody molecules of the present invention, including eukaryotic cells, e.g., mammalian cells, insect cells, yeast cells; and prokaryotic cells, e.g., *Escherichia coli* cells. Host cells include cultured cells as well as cells within transgenic animals, transgenic plants or cultured plant tissues or animal tissues. The term "recombinant host cell" encompasses a host cell different from the parent cell upon introduction of a recombinant nucleic acid molecule, recombinant expression vector, or circRNA, and is specifically achieved by transformation. A host cell of the present disclosure can be a prokaryotic cell or a eukaryotic cell, as long as the cell is capable of introducing the recombinant nucleic acid molecule, recombinant expression vector, or circRNA, etc. of the present disclosure.

As used in the present disclosure, the term "individual", "patient", or "subject" includes mammals. Mammals include, but are not limited to, domestic animals (e.g., cows, sheep, cats, dogs, and horses), primates (e.g., humans and non-human primates such as monkeys), rabbits, and rodents (e.g., mice and rats).

As used in the present disclosure, the term "transformation, transfection, and transduction" has the meanings commonly understood by those skilled in the art, i.e., a process of introducing exogenous DNA into a host. The methods of transformation, transfection, and transduction include any method of introducing a nucleic acid into a cell, including, but not limited to, electroporation, calcium phosphate ($CaPO_4$) precipitation, calcium chloride ($CaCl_2$) precipitation, microinjection, polyethylene glycol (PEG) method, DEAE-dextran method, cationic liposome method, and lithium acetate-DMSO method.

As used in the present disclosure, "treatment" or "treating" refers to: contacting (e.g., administering) a subject with circRNA, circularized precursor RNA, composition, etc. of the present invention after suffering from a disease, thereby reducing symptoms of the disease as compared with not contacting, and does not necessarily mean that the symptoms of the disease must be completely suppressed. Suffering from a disease means that: a body has symptoms of the disease.

As used in the present disclosure, "prevention", "preventing" refer to: contacting (e.g., administering) a subject with a circular RNA, composition, etc. of the present invention prior to suffering from a disease, thereby reducing symptoms after suffering from the disease as compared with not contacting, and does not mean that it is necessary to completely suppress the disease.

As used in the present disclosure, the term "effective amount" refers to an amount or dose of the recombinant nucleic acid molecule, recombinant expression vector, circularized precursor RNA, circular RNA, vaccine or composition of the invention that, upon single or multiple dose administration to a patient, produces the desired effect in the patient in need of treatment or prevention. An effective amount can be readily determined by the attending physician, as one skilled in the art, by considering a variety of factors: species such as mammals; its size, age and general health; specific disease involved; extent or severity of disease; individual patient's response; specific antibody administered; mode of administration; bioavailability characteristics of the administered formulation; selected dosing regimen; and use of any concomitant therapy.

As used in the present disclosure, the term "individual", "patient", or "subject" includes mammals. Mammals include, but are not limited to, domestic animals (e.g., cows, sheep, cats, dogs, and horses), primates (e.g., humans and non-human primates such as monkeys), rabbits, and rodents (e.g., mice and rats).

Unless defined otherwise or clearly indicated by the context, all technical and scientific terms in the present disclosure have the same meaning as commonly understood by a person with ordinary skill in the art to which the present disclosure belongs.

Clean PIE System

Figure 18:
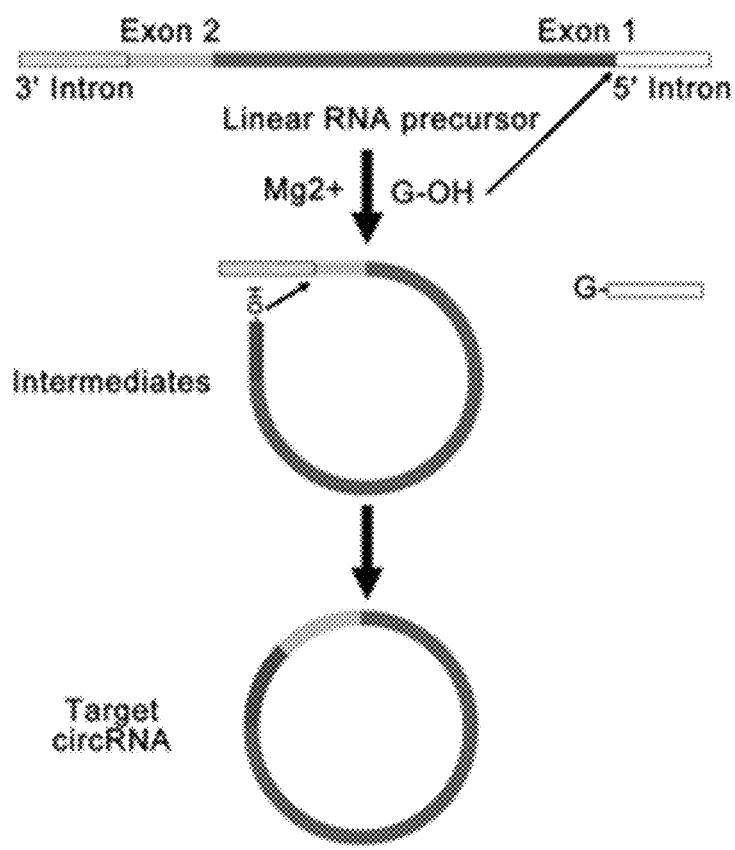
FIG. 18 shows a schematic of circularization of a classic PIE system to form circRNA.

A process of ligating a conventional PIE system to form circRNA is shown in FIG. 18, wherein the linear RNA includes the following elements linked in sequence: 3' intron, second exon E2 (Exon 2), exogenous fragments, first exon E1 (Exon 1) and 5' intron. When GTP and $Mg^{2+}$ are present in the environment, GTP attacks the linking position between E1 and the 5' intron, resulting in breaking of a 5' splicing site (5ss) and, release of the 5' intron; then the 3'-OH end of E1 attacks the linking position of the 3' intron and E2, resulting in breaking of 3' splicing site (3ss) break and release of the 3' intron; and finally, a target circRNA is formed by ligation.

However, the use of a conventional PIE system will result in the presence of additional E1 and E2 exon sequences in circRNA and reduced sequence accuracy of circRNA, thereby resulting in increased natural immunogenicity of circRNA and susceptibility to degradation in cells.

In order to solve the above problems, the present disclosure provides a Clean PIE system with a novel structure. The Clean PIE system can be used to prepare circRNA by using the self-splicing of the PIE system without changing the protein expression sequence, and has a high circularization efficiency. Furthermore, no additional E1 and E2 sequences need to be introduced into circRNA after circularization, which not only simplifies a structure of circRNA, but also reduces potential safety hazards. The Clean PIE system can also improve sequence accuracy of circRNA, reduce natural immunogenicity of circRNA and improve its intracellular stability. It is suitable for gene therapy vectors, expression of therapeutic proteins, nucleic acid vaccines and other clinical applications, and has broad application prospects.

In the present disclosure, the Clean PIE system includes, but is not limited to, a DNA construct for preparing circRNA, a recombinant expression vector including the DNA construct, a circularized precursor RNA molecule obtained by in vitro transcription using the recombinant expression vector, and the like.

In some embodiments, the present disclosure provides a recombinant nucleic acid molecule for preparing circRNA. Illustratively, the recombinant nucleic acid molecule can be the DNA construct for preparing circRNA, a circularized precursor RNA molecule, etc. as described above.

In some embodiments, the recombinant nucleic acid molecule has a structure shown in FIG. 2A, in the 5' to 3' direction, including elements arranged in the following order: intron fragment II, truncated fragment II of the translational initiation element, a coding element encoding at least one target polypeptide, truncated fragment I of the translation initiation element, and intron fragment I.

Among them, the 3' end of the truncated fragment I of the translation initiation element includes a ribozyme recognition site I consisting of a first predetermined number of nucleotides located at the 3' end of the truncated fragment I of the translation initiation element; and the 5' end of the truncated fragment II of the translational initiation element includes a ribozyme recognition site II consisting of a second predetermined number of nucleotides located at the 5' end of the truncated fragment II of the translational initiation element.

The nucleotide sequence of the truncated fragment I of the translation initiation element and the nucleotide sequence of the truncated fragment II of the translational initiation element are used to form a translation initiation element sequence in the 5' to 3' direction; the nucleotide sequence of the truncated fragment I of the translation initiation element corresponds to a partial sequence of the translation initiation element sequence near the 5' direction, and the nucleotide sequence of the truncated fragment II of the translational initiation element corresponds to the remaining partial sequence of the translation initiation element sequence near the 3' direction;

The nucleotide sequence of the intron fragment I and the nucleotide sequence of the intron fragment II form an intron sequence in the 5' to 3' direction; the nucleotide sequence of the intron fragment I includes a partial sequence of the intron sequence near the 5' direction, and the nucleotide sequence of the intron fragment II includes the remaining partial sequence of the intron sequence near the 3' direction.

That is, the nucleotide sequence of the truncated fragment I of the translation initiation element is ligated to the nucleotide sequence of the truncated fragment II of the translational initiation element to obtain a translation initiation element sequence, and the nucleotide sequence of the intron fragment I is ligated to the nucleotide sequence of the intron fragment II to obtain an intron sequence. When a recombinant nucleic acid molecule having the above structure is used for preparing circRNA, the linking position of the ribozyme recognition site I and the intron fragment I first breaks to release the intron fragment I; and the linking position of the ribozyme recognition site II and the intron fragment II then breaks to release the intron fragment II. The 3' end of the truncated fragment I of the translation initiation element is ligated to the 5' end of the truncated fragment II of the translational initiation element to form a circular molecule. In the present disclosure, without changing the target polypeptide sequence encoded by the coding region, and without additionally introducing E1 and E2 sequences, circRNA encoding the target protein can be obtained by self-splicing, which has high sequence accuracy, stability, and low immunogenicity.

Meanwhile, since the ribozyme recognition site I and the ribozyme recognition site II are arranged inside the translation initiation element truncated fragments, no additional E1 and E2 sequences need to be introduced into circRNA after circularization in vitro, providing advantages of accurate sequence, simple structure, low immunogenicity, and the like, enabling large-scale in vitro production with the application advantages in the fields of nucleic acid vaccines, expression of therapeutic proteins, clinical immunotherapy, and the like.

Translation Initiation Element

In the present disclosure, the translation initiation element may be any type of element capable of initiating translation of a target polypeptide. In some embodiments, the translation initiation element is an element including any one or two or more of the following sequences: an IRES sequence, a 5'UTR sequence, a Kozak sequence, a sequence with $m^6A$ modification (N(6)methyladenosine modification), and a complementary sequence of ribosomal 18S rRNA. In other embodiments, the translation initiation element may also be any other type of cap-independent translation initiation element.

In some embodiments, the translation initiation element is an IRES element, and the IRES element is derived from, but not limited to, viruses, mammals, drosophila, and the like. In some alternative embodiments, the IRES element is derived from a virus. Illustratively, the IRES element includes an IRES sequence from a small RNA virus. Further, IRES elements include, but are not limited to, an IRES sequence derived from Echovirus, Human poliovirus, Human Enterovirus, Coxsackievirus, Human rhinovirus, Canine picornavirus, Turdivirus 3, Hepatovirus, Passerivirus, Picornaviridae, Tremovirus A, Feline kobuvirus, Murine kobuvirus, Kobuvirus sewage Kathmandu, Ferret kobuvirus, Marmot kobuvirus, Human parechovirus, Chicken picornavirus, Falcon picornavirus, Feline picornavirus, French Guiana picornavirus, and the like.

In some alternative embodiments, the recombinant nucleic acid molecules provided by the present disclosure, in the 5' to 3' direction, consist of the following elements: intron fragment II, truncated fragment II of the translational initiation element, a coding element encoding at least one target polypeptide, truncated fragment I of the translation initiation element, and intron fragment I. In some other alternative embodiments, the recombinant nucleic acid molecule may also include any other one or more than two elements, for example, a transcriptional regulatory element for regulating transcription level, a translational regulatory element for regulating translation level, a purification element for purifying the prepared circRNA, and the like.

Intron Fragment

The intron fragments in the present disclosure are derived from Group I intron which has ribozyme activity for self-splicing reactions and is widely present in various species. Illustratively, the Group I intron includes, but is not limited to, T4 phage td gene, *Anabaena* tRNALeu, TpaCOX2, Ptu, and the like.

In some embodiments, the intron fragment I and the intron fragment II are derived from Group I intron and include a partial sequence near the 5' direction and a partial sequence near the 3' direction, respectively, constituting the Group I intron. The ribozyme recognition site I is derived from the exon sequence (Exon 1, E1) ligated to the 5' end of the Group I intron, and the ribozyme recognition site II is derived from the exon sequence (Exon 2, E2) ligated to the 3' end of the Group I intron. The intron fragment I is ligated to the ribozyme recognition site I, and the intron fragment II is ligated to the ribozyme recognition site II, constituting a PIE system capable of self-splicing.

In some alternative embodiments, the ribozyme recognition site I consists of 3 to 100 nucleotides, preferably 3 to 50 nucleotides, and more preferably 3 to 10 nucleotides. That is, the first predetermined number of nucleotides at the 3' end of the truncated fragment I of the translation initiation element is 3 to 100 nucleotides, preferably 3 to 50 nucleotides, and more preferably 3-10 nucleotides. Illustratively, the first predetermined number is 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, and any integer value therebetween.

In some alternative embodiments, the ribozyme recognition site II consists of 1 to 100 nucleotides, preferably 1 to 50 nucleotides, and more preferably 1 to 10 nucleotides. That is, the second predetermined number of nucleotides at the 5' end of the truncated fragment II of the translational initiation element is 1 to 100 nucleotides, preferably 1 to 50 nucleotides, and more preferably 1 to 10 nucleotides. Illustratively, the first predetermined number is 1, 2, 3, 4, 5, 6, 7, 8, 9, 10, 15, 20, 25, 30, 35, 40, 45, 50, 55, 60, 65, 70, 75, 80, 85, 90, 95, 100, and any integer value therebetween.

In some preferred embodiments, the sum of the first predetermined number and the second predetermined number is not equal to 3y, y≥1 and y is an integer. That is, the sum of the first predetermined number and the second predetermined number is not equal to an integer multiple of 3. When the sum of the two is not an integer multiple of 3, degree of freedom for arranging ribozyme recognition sites in the coding region can be increased to achieve efficient looping of circRNA.

Figure 15:
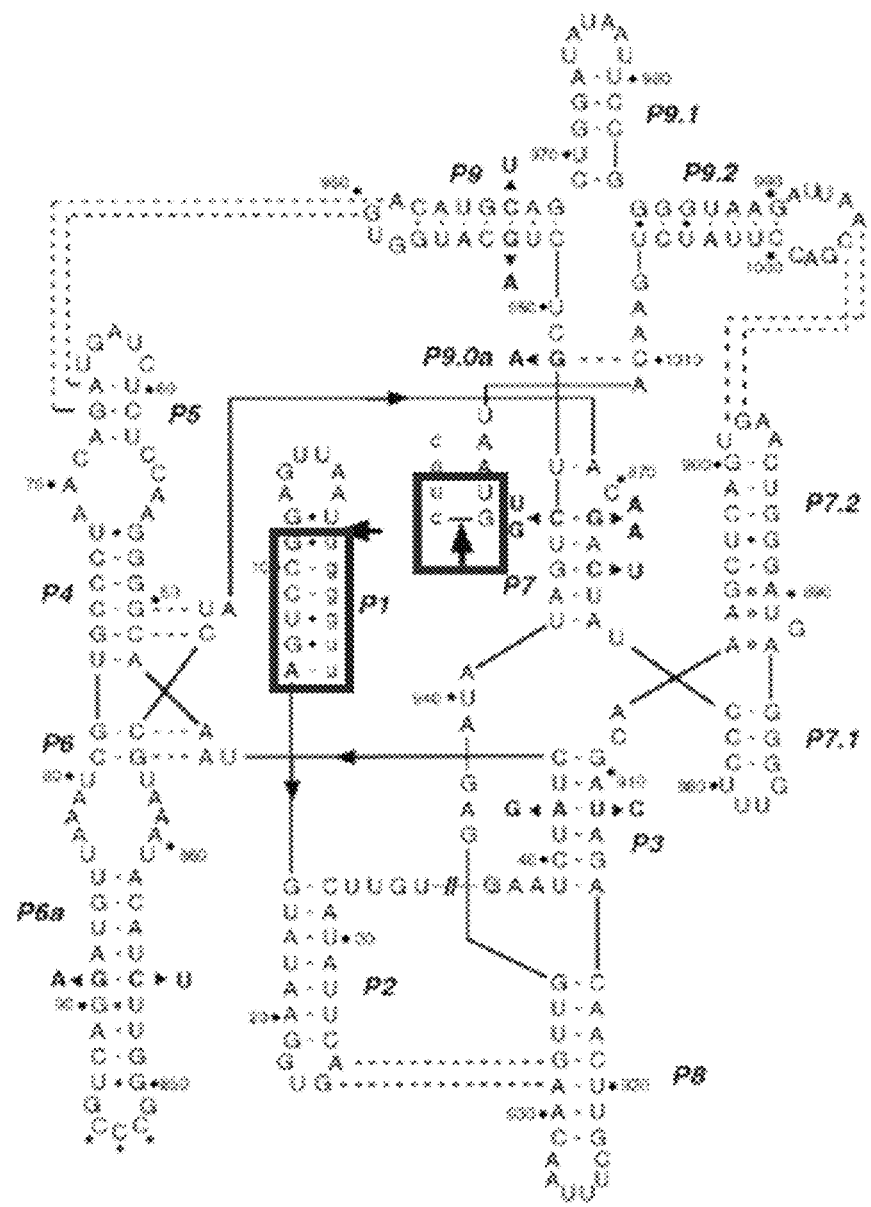
FIG. 15 shows a secondary structure prediction diagram derived from T4td intron.

In some alternative embodiments, the Group I intron is T4 td intron derived from the td gene of T4 phage, the secondary structure of which is shown in FIG. 15. The ribozyme recognition site for circularization in the T4 td intron has a nucleotide sequence of "5'-TTGGGTCT-3'", wherein the circularization position is between T and C. Therefore, the ribozyme recognition site I has a nucleotide sequence of "5'-TTGGGT-3'" and the ribozyme recognition site II has a nucleotide sequence of "5'-CT-3'".

It should be noted that, ribozyme recognition sites with a small number of base mutations can also be used for circRNA in vitro, under conditions that the bases at the circularization position are unchanged. Illustratively, the present disclosure finds that ribozyme recognition sites and their linked intron fragments retain circularization activity when one or more than two of the following mutations are present in "5'-TTGGGTCT-3'": base T at position 2 is mutated to C, base G at position 3 is mutated to A, and base T at position 8 is mutated to A.

In some alternative embodiments, the intron fragment I derived from T4 td intron has a nucleotide sequence as set forth in SEQ ID NO: 20, or a sequence having 80%, 81%, 82%, 83%, 84%, 85%, 86%, 87%, 88%, 89%, 90%, 91%, 92%, 93%, 94%, 95%, 96%, 97%, 98% and 99% sequence identity to the nucleotide sequence set forth in SEQ ID NO: 20.

In some alternative embodiments, the intron fragment II derived from T4 td intron has a nucleotide sequence as set forth in SEQ ID NO: 19 or a sequence having 80%, 81%, 82%, 83%, 84%, 85%, 86%, 87%, 88%, 89%, 90%, 91%, 92%, 93%, 94%, 95%, 96%, 97%, 98% and 99% sequence identity to the nucleotide sequence set forth in SEQ ID NO: 19.

Figure 16:
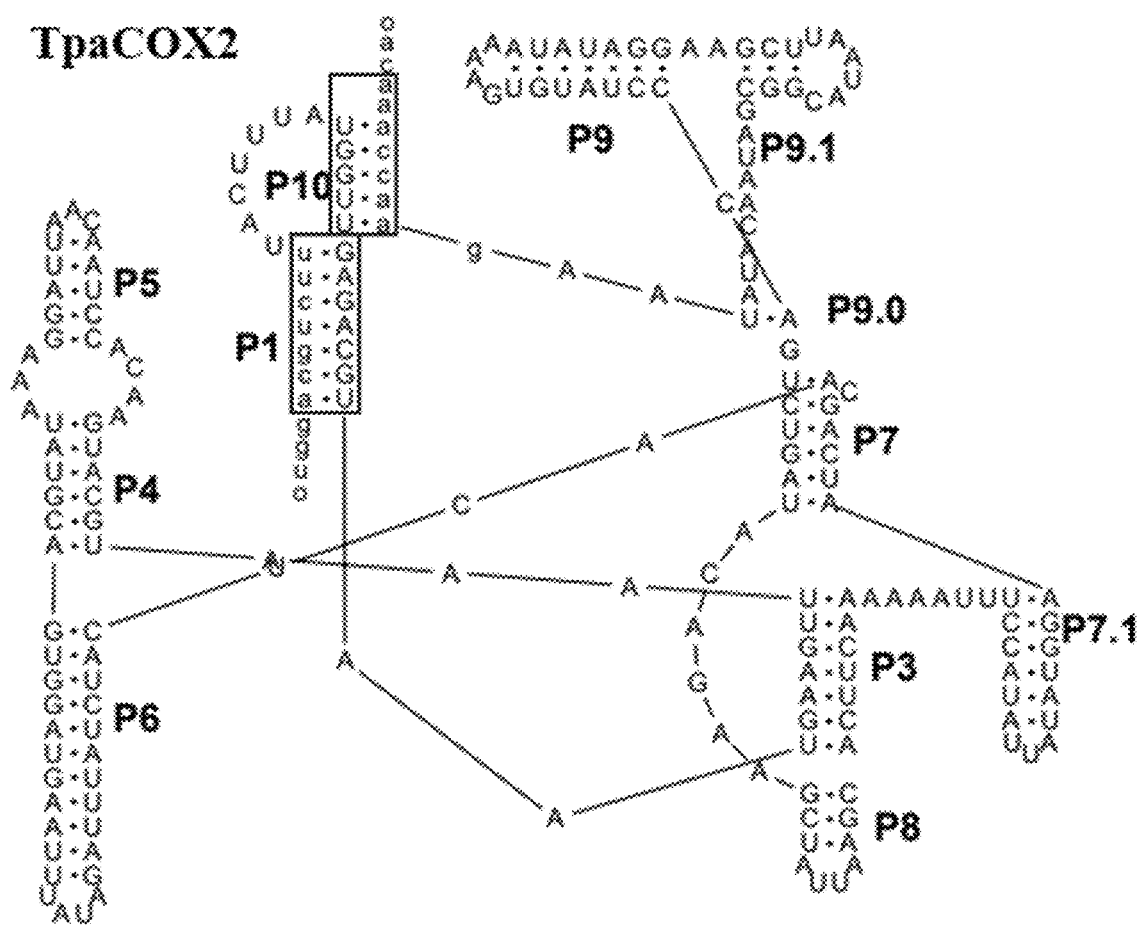
FIG. 16 shows a secondary structure prediction diagram derived from TpaCOX2 intron.

In some alternative embodiments, the Group I intron is TpaCOX2 intron. The TpaCOX2 intron is an intron sequence of cytochrome oxidase subunit cox2 gene of *T. papilionaceus* mitochondria, the secondary structure of which is shown in FIG. 16. The ribozyme recognition site for circularization in TpaCOX2 intron has a nucleotide sequence of "5'-ACGTCTTAACCAA-3'", wherein the circularization position is between T and A. Therefore, the ribozyme recognition site I has a nucleotide sequence of "5'-ACGTCTT-3'", and the ribozyme recognition site II has a nucleotide sequence of "5'-AACCAA-3'".

Figure 17:
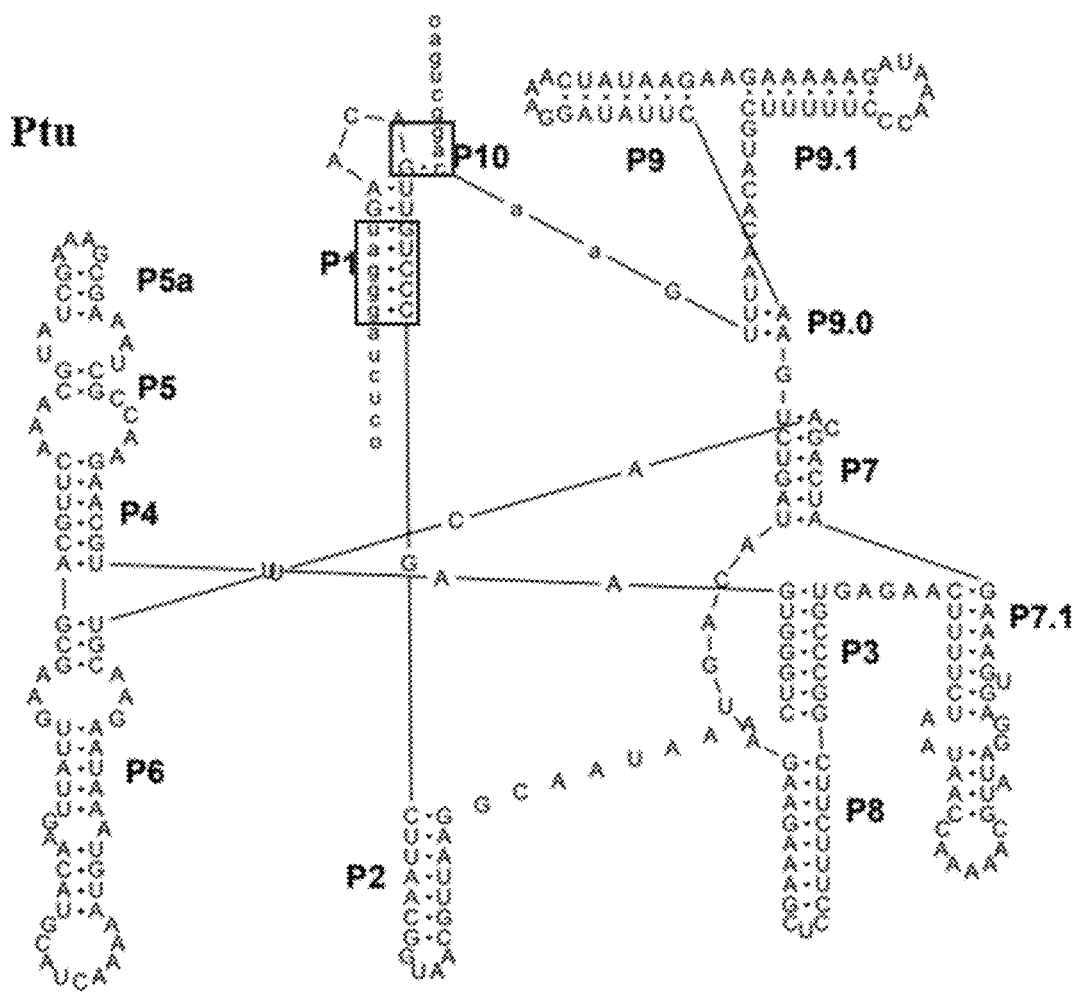
FIG. 17 shows a secondary structure prediction diagram derived from Ptu intron.

In some alternative embodiments, the Group I intron is Ptu intron, the secondary structure of which is shown in FIG. 17. Ptu is a precursor RNA of chloroplast ribosomal large subunit RNA (rrnL) in *Pedinomonas tuberculata*. *Pedinomonas tuberculata* is a green algae of the family Pseudomonadaceae. The ribozyme recognition site for circularization in Ptu intron has a nucleotide sequence of "5'-AGGGATCA-3'", wherein the circularization position is between T and C. Therefore, the ribozyme recognition site I has a nucleotide sequence of "5'-AGGGAT-3'", and the ribozyme recognition site II has a nucleotide sequence of "5'-CA-3'".

It should be noted that, in the present disclosure, sequences of ribozyme recognition site and intron fragments are not restrictively defined, as long as they are derived from Group I intron and can be efficiently circularized to produce circRNA in vitro.

Recombinant Nucleic Acid Molecule Containing Insertion Element

In some embodiments, the recombinant nucleic acid molecule includes an insertion element that can be used to regulate transcription of the recombinant nucleic acid molecule, to regulate translation of circRNA, to achieve specific expression of circRNA between different types of tissue, or to purify circRNA, etc. Illustratively, as shown in FIG. 2B, the insertion element is located between the coding element and the truncated fragment I of the translation initiation element.

In some embodiments, the insertion element is at least one selected from the group consisting of (i)-(iii): (i) a transcriptional level regulatory element, (ii) a translational level regulatory element, and (iii) a purification element. Illustratively, the insertion element includes one or a combination of any two or more of the following sequences: an untranslated region (UTR) sequence, a polyN sequence, an aptamer sequence, a riboswitch sequence, and a transcription regulatory factor-binding sequence; and in the polyN sequence, N is selected from at least one of A, T, G and C.

In some alternative embodiments, the translational regulatory element includes an untranslated region sequence that can be used to regulate stability, immunogenicity, and efficiency of circRNA in expressing a target polypeptide, and the like. In the present disclosure, the untranslated region sequence is not particularly defined, and may be selected from any type of sequence known in the art having the properties of regulating circRNA transcription, translation, intracellular stability, immunogenicity, and the like. Further, the untranslated region sequence is not limited to a 5'UTR sequence or a 3' UTR sequence.

In some alternative embodiments, the untranslated region sequence includes one or more miRNA recognition sequences, e.g., 1, 2, 3, 4, 5, 6 and 7 miRNA recognition sequences. By adding one or more miRNA recognition sequences, specific expression of circRNA in different types of tissue and different cells can be realized, and targeted delivery of the circRNA molecule can be achieved.

In some alternative embodiments, the translational regulatory element includes a polyN sequence, wherein N may be at least one of A, T, G, and C. A translational regulatory element including a polyN sequence can be added to improve efficiency of circRNA in expressing a target polypeptide, improve immunogenicity and stability, etc., or purify circRNA. In the present disclosure, the length of the polyN sequence, the type of N selected in the polyN sequence, and the manner of composition are not specifically defined, as long as they are advantageous to improved performance of circRNA. Illustratively, the polyN sequence is a polyA sequence, a polyAC sequence, and the like.

In some alternative embodiments, the translational regulatory element includes a riboswitch sequence. The riboswitch sequence is a class of untranslated sequences that regulate transcription and translation of RNA. In the present disclosure, the riboswitch sequence can affect expression of circRNA, including, but not limited to, transcription termination, inhibition of translation initiation, mRNA self-cleavage, and alterations in the splicing pathway in eukaryotes. In addition, the riboswitch sequence may also control expression of circRNA by triggering binding or removal of molecules. Illustratively, the riboswitch sequence is cobalamin riboswitch (also known as B12-element), FMN riboswitch (also known as RFN element), glmS riboswitch, SAM riboswitch, SAH riboswitch, tetrahydrofolate riboswitch, Moco riboswitch, and the like, and in the present disclosure, the riboswitch type and sequence are not defined, as long as the riboswitch can regulate the transcription and translation levels of circRNA in expressing a target polypeptide.

In some alternative embodiments, the translational regulatory element includes an aptamer sequence. In the present disclosure, the aptamer sequence can be used to regulate transcription and translation of circRNA, or used for in vitro purification and preparation of circRNA.

Recombinant Nucleic Acid Molecule Containing Homologous Arm

In some embodiments, the recombinant nucleic acid molecule includes a homologous arm. Specifically, the homologous arm includes a 5' homologous arm at the 5' end of the recombinant nucleic acid molecule and a 3' homologous arm at the 3' end of the recombinant nucleic acid molecule, and the nucleic acid sequence of the 5' homologous arm hybridizes to the nucleotide sequence of the 3' homologous arm.

Figure 1:
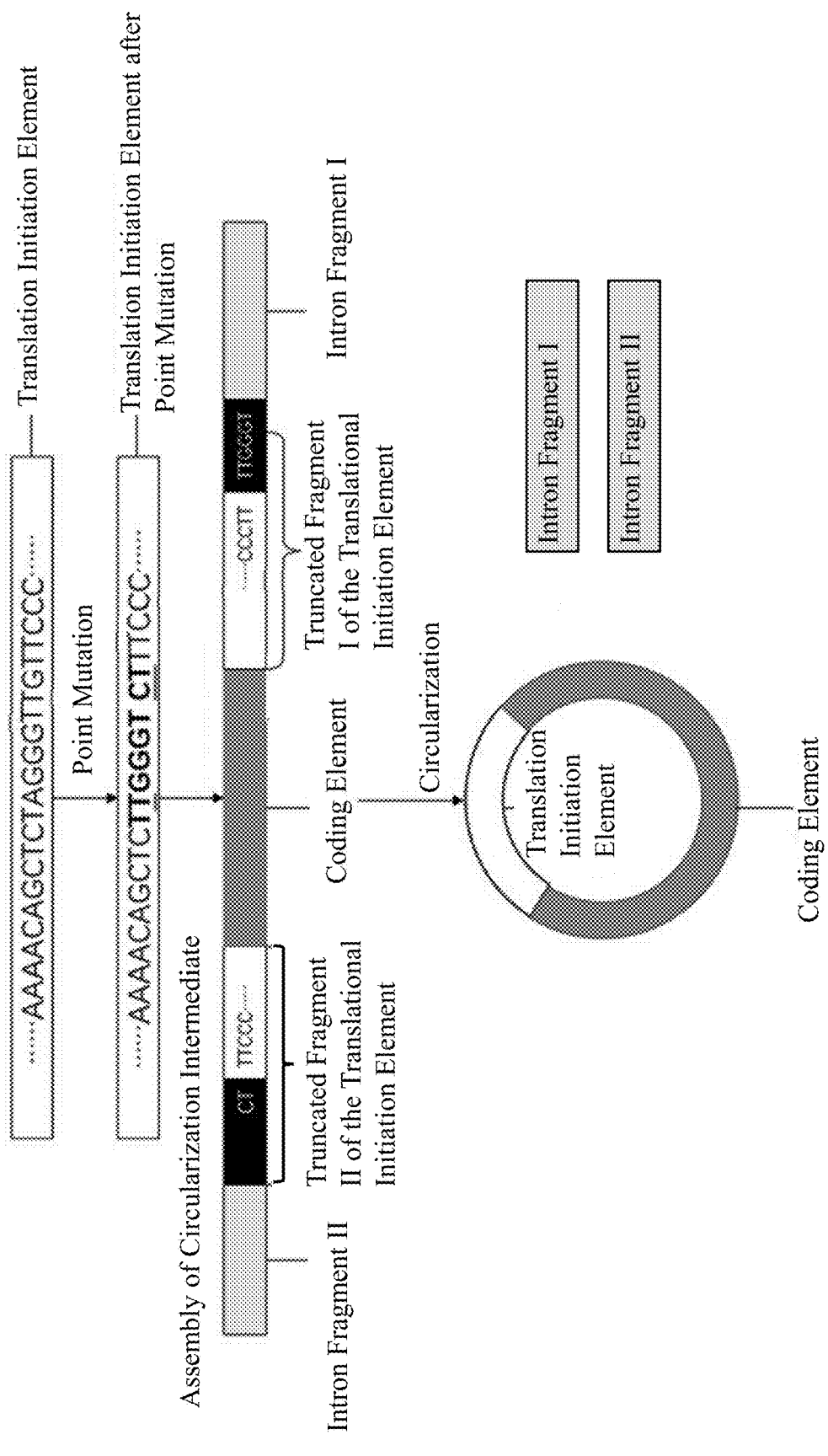
FIG. 1 shows a self-assembly process of the Clean PIE system of the present disclosure for preparation of circRNA in vitro.
Figures 2A, 2B, 2C:
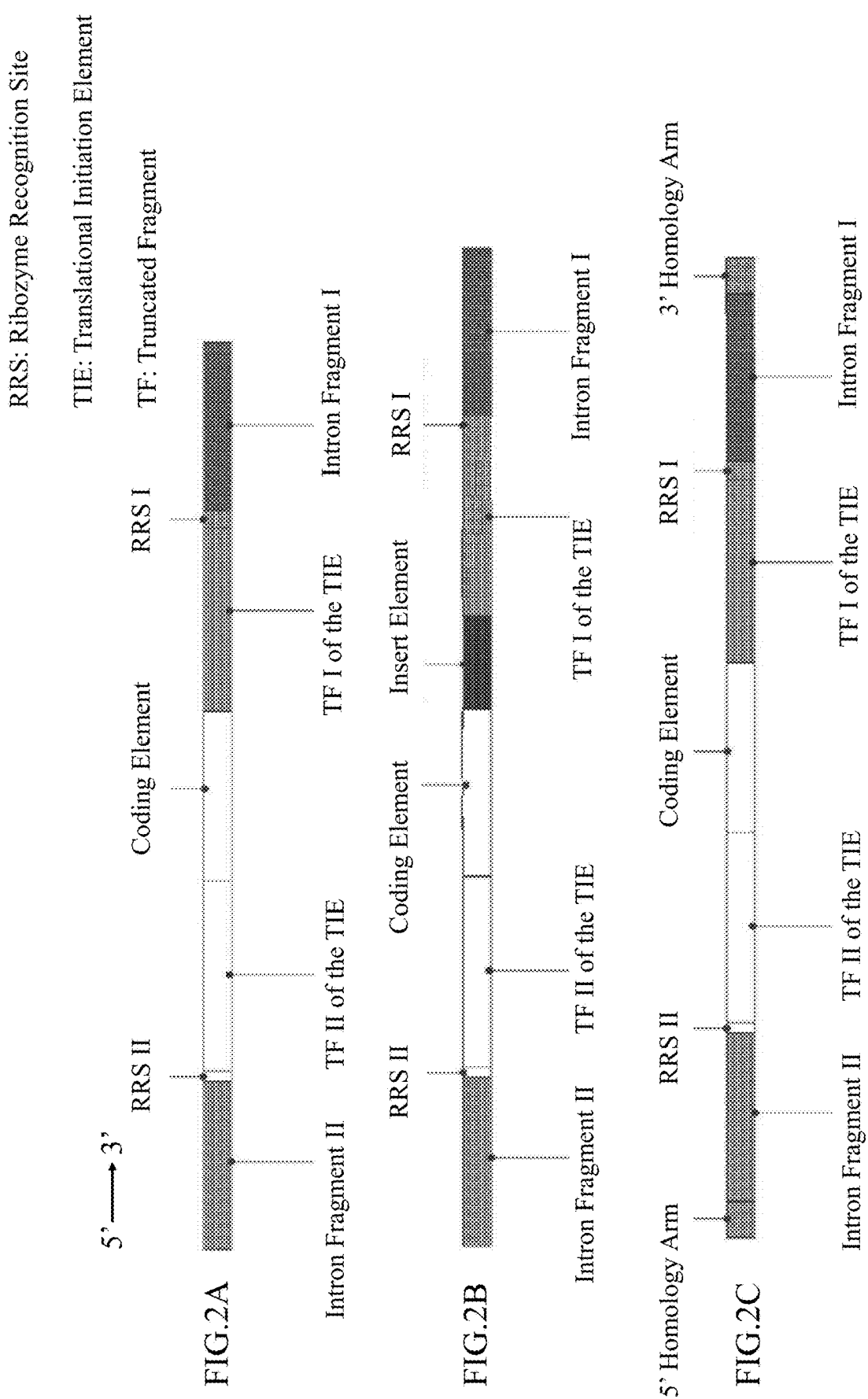
FIGS. 2A through 2C shows a structural schematic diagram of a recombinant nucleic acid molecule (Clean PIE system) for preparation of circRNA of the present disclosure.

In some embodiments, as shown in FIG. 2C, in the recombinant nucleic acid molecule, the 5' homologous arm is ligated to the 5' end of the intron fragment II and the 3' homologous arm is ligated to the 3' end of the intron fragment I. The sequences of the 5' homologous arm and the 3' homologous arm hybridize, so that the intron fragment I and the intron fragment II are close to each other, and after the linking position of the ribozyme recognition site I and the intron fragment I is broken, the 3'-OH of the ribozyme recognition site I further attacks a phosphodiester bond linking the ribozyme recognition site II to the intron fragment II so as to release the intron fragment II.

Target Polypeptides

In the present disclosure, the type of target polypeptide is not restrictively defined, which may be human-derived or non-human-derived. Exemplary target polypeptides include, but are not limited to, antigens, antibodies, antigen-binding fragments, fluorescent proteins, proteins with therapeutic activity against diseases, proteins with gene editing activity, and the like.

In the present disclosure, the term "antibody" is used in the broadest sense, refers to a protein including an antigen binding site and encompasses natural and artificial antibodies of various structures, including, but not limited to, monoclonal antibodies, polyclonal antibodies, multispecific antibodies (e.g., bispecific antibodies), single chain antibodies, intact antibodies, and antibody fragments.

In the present disclosure, the term "antigen-binding fragment" is a portion or fragment of an intact or complete antibody that has fewer amino acid residues than the intact or complete antibody, and is capable of binding to an antigen or competing with an intact antibody (i.e., with the intact antibody from which the antigen-binding fragment is derived) for binding to an antigen. Antigen-binding fragments can be prepared by recombinant DNA technology, or by enzymatic or chemical cleavage of intact antibodies. Antigen binding fragments include, but are not limited to, Fv, Fab, Fab', Fab'-SH, F(ab')2; diabodies; linear antibodies; single chain antibodies (e.g., scFvs); single domain antibodies; bivalent or bispecific antibodies or fragments thereof; camelid antibodies (heavy chain antibodies); and bispecific or multispecific antibodies formed from antibody fragments.

In the present disclosure, proteins with therapeutic activity against diseases may include, but are not limited to, enzyme replacement proteins, proteins for supplementation, protein vaccines, antigens (e.g., tumor antigens, viruses, bacteria), hormones, cytokines, antibodies, immunotherapies (e.g., for cancer), cell reprogramming/transdifferentiation factors, transcription factors, chimeric antigen receptors, transposases or nucleases, immune effectors (e.g., affecting susceptibility to immune responses/signals), regulated death effector proteins (e.g., inducers of apoptosis or necrosis), non-soluble inhibitors of tumors (e.g., oncoprotein inhibitors), epigenetic modifiers, epigenetic enzymes, transcription factors, DNA or protein-modifying enzymes, DNA intercalators, efflux pump inhibitors, nuclear receptor activators or inhibitors, proteasome inhibitors, enzyme competitive inhibitors, protein synthesis effectors or inhibitors, nucleases, protein fragments or domains, ligands or receptors, and CRISPR systems or components thereof, and the like.

Coding Element Containing Tandem Coding Region

In some embodiments, the recombinant nucleic acid molecule includes a coding element, and the coding element includes at least one coding region. Illustratively, the coding element includes 1, 2, 3, 4, 5, 10, 15, 20 or 25 coding regions, etc. In some alternative embodiments, optionally, the coding element includes at least two coding regions, and each coding region independently encodes any type of target polypeptide.

In some alternative embodiments, the coding element includes two or more coding regions. As shown in FIGS. 3A and 3B, the recombinant nucleic acid molecule includes elements arranged in the following order in the 5' to 3' direction: intron fragment II, truncated fragment II of the translational initiation element, at least two coding regions, truncated fragment I of the translation initiation element, and intron fragment I. In still other alternative embodiments, the recombinant nucleic acid molecule consists of the elements arranged in the order described above.

In some preferred embodiments, the coding element further includes a linker between any two adjacent coding regions. The adjacent coding regions are separated by the linker to enable expression of two or more target polypeptides by circRNA prepared from the recombinant nucleic acid molecule.

In the present disclosure, the linker may be a polynucleotide encoding a 2A peptide, or other types of polynucleotides encoding a linker peptide for spacing target polypeptides. Among them, the 2A peptides are short peptides (about 18 to 25 amino acids in length) derived from viruses and are commonly referred to as "self-cleaving" peptides, enabling the production of multiple proteins from a transcript. Illustratively, the 2A peptide is P2A, T2A, E2A, F2A, and the like.

In the present disclosure, each coding region encompassed by the coding element independently encodes any type of target polypeptide. Among them, target polypeptides encoded by any two coding regions may be the same or different.

Coding Element Containing at Least 1 Translation Initiation Element

In some embodiments, the coding element includes at least two coding regions, wherein a translation initiation element is linked between any two adjacent coding regions. Illustratively, the coding element includes 1, 2, 3, 4, 5, 10, 15, 20 or 25 coding regions, etc. Also, within the coding element, a translation initiation element is arranged between any two adjacent coding regions. In this manner, expression of two or more target polypeptides can be achieved by ligating a translation initiation element upstream of each coding region in circRNA prepared in vitro from the recombinant nucleic acid molecule.

In some alternative embodiments, the coding element includes two or more coding regions. As shown in FIGS. 4A and 4B, the recombinant nucleic acid molecule includes elements arranged in the following order in the 5' to 3' direction: intron fragment II, truncated fragment II of the translational initiation element, at least two coding regions, truncated fragment I of the translation initiation element, and intron fragment I. Among them, a translation initiation element is linked between any two adjacent coding regions. In still other alternative embodiments, the recombinant nucleic acid molecule consists of the elements arranged in the order described above.

In the present disclosure, the translation initiation element may be any type of element capable of initiating translation of a target polypeptide. In some embodiments, the translation initiation element is an element including any one or more than two of the following sequences: an IRES sequence, a 5'UTR sequence, a Kozak sequence, a sequence with $m^6A$ modification (N(6)methyladenosine modification), and a complementary sequence of ribosomal 18S rRNA. In other embodiments, the translation initiation element may also be any other type of cap-independent translation initiation element.

In the present disclosure, each coding region encompassed by the coding element independently encodes any type of target polypeptide. The target polypeptides encoded by any two coding regions may be the same or different.

In the circRNA prepared by using the above recombinant nucleic acid molecule, one translation initiation element is correspondingly ligated to the 5' end of each coding region, and multiple coding regions are in tandem via multiple translation initiation elements to realize expression of at least two target polypeptides.

Recombinant Expression Vector Containing Recombinant Nucleic Acid Molecule

In some embodiments, the recombinant nucleic acid molecule is present as part of a recombinant expression vector used to prepare circRNA. During in vitro transcription and circularization, circRNA expressing a target polypeptide can be prepared.

In other embodiments, the recombinant nucleic acid molecule can also be present as a circularized precursor RNA molecule, or a part thereof, obtained after linearization and transcription reaction of the recombinant expression vector. That is, the recombinant nucleic acid molecule needs only undergo a circularization reaction to obtain circRNA expressing a target polypeptide.

In some embodiments, steps of preparing circRNA in vitro includes:

transcription step: transcribing the recombinant nucleic acid molecule as described in the present disclosure or the recombinant expression vector according to the present disclosure to form a circularized precursor nucleic acid molecule; and circularization step: subjecting the circularized precursor nucleic acid to a circularization reaction to give circRNA.

In some alternative embodiments, the method further includes a step of purifying the circRNA.

CircRNA

In some embodiments, the circRNA of the present disclosure is prepared using the Clean PIE system provided by the present disclosure, including the elements, in the 5' to 3' direction, arranged in the following order: a translation initiation element, and a coding element for encoding at least one target polypeptide.

Figure 5B:
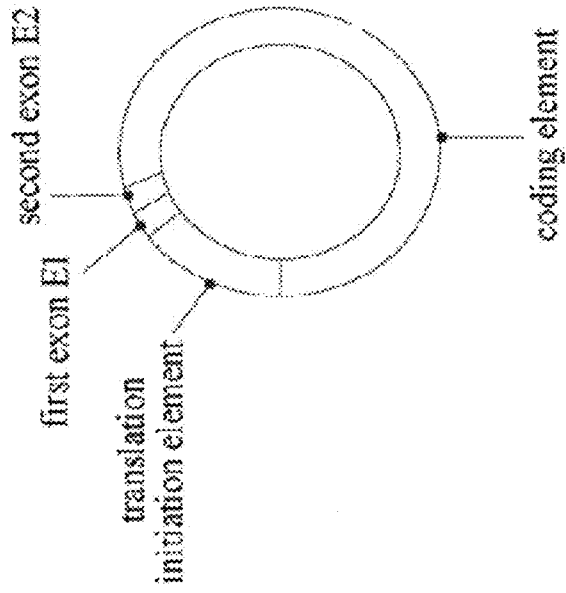
FIGS. 5A and 5B show a circRNA structure, wherein 5A shows a structure of circRNA prepared using the Clean PIE system of the present disclosure, and 5B shows a structure of circRNA prepared using a conventional PIE system.
Figure 5A:
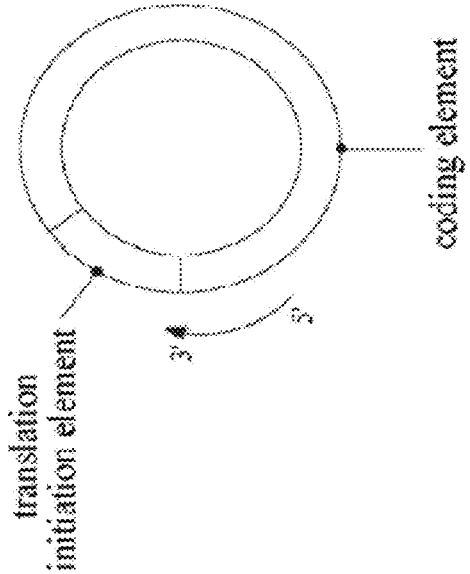

Compared with circRNA prepared by a traditional PIE system as shown in FIG. 5B, circRNA prepared by using the clean PIE system in the present disclosure does not introduce additional E1 and E2 sequences (FIG. 5A) under the condition of ensuring integrity of the protein coding sequence, so as to ensure accuracy of the sequence and secondary structure of the circRNA, reduce natural immunogenicity of the circRNA and improve its intracellular stability, is suitable for clinical application fields such as gene therapy vector, expression of therapeutic protein and nucleic acid vaccines, and has broad application prospects.

In some embodiments, the coding element of the circRNA includes at least one coding region, and each coding region independently encodes any type of target polypeptide, the circRNA being capable of encoding one or more target polypeptides in tandem. Illustratively, the circRNA expresses 1, 2, 3, 4, 5, 10, 15, 20 or 25 target polypeptides, etc.

As a preferred embodiment, any two adjacent coding regions are linked by a linker, and the target polypeptides encoded by the adjacent coding regions are separated by a linking peptide encoded by the linker, so that the same circRNA can express two or more target polypeptides in tandem.

Figures 6A, 6B:
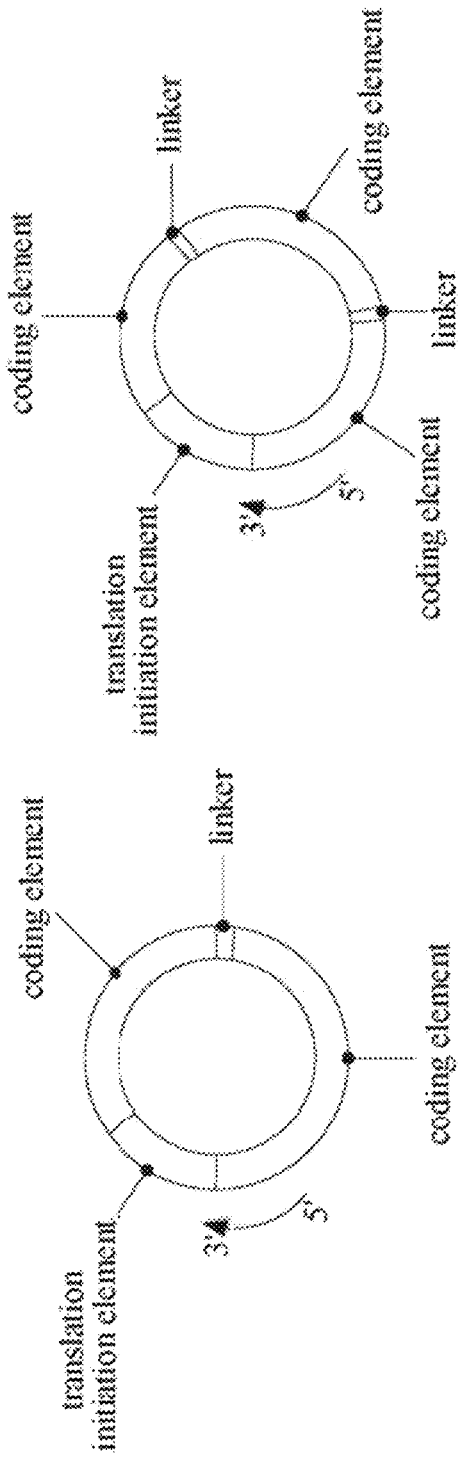
FIGS. 6A and 6B show a circRNA structure prepared using the Clean PIE system of the present disclosure.

In some alternative embodiments, the coding element of the circRNA includes two or more coding regions. Illustratively, as shown in FIGS. 6A and 6B, in the 5' to 3' direction, the circRNA includes a translation initiation element, and a coding element including at least two coding regions, wherein a linker is linked between any two adjacent coding regions in the coding element. The linker separates two adjacent coding regions so that the circRNA can express at least two target polypeptides in tandem in a cell. In still other alternative embodiments, the circRNA consists of elements arranged in the above order.

In some embodiments, the coding element of the circRNA includes at least two coding regions, wherein a translation initiation element is linked between any two adjacent coding regions. Illustratively, 1, 2, 3, 4, 5, 10, 15, 20 or 25 coding regions and so on are contained in the coding element. Transcription of different coding regions may be initiated by a translation initiation element linked at the 5' end of each coding region, enabling the same circRNA to be used to encode two or more target polypeptides.

In some alternative embodiments, as shown in FIGS. 7A and 7B, the circRNA includes, in the 5' to 3' direction: a translation initiation element, at least two coding regions, and a translation initiation element linked between any two adjacent coding regions. Therefore, the circRNA contains at least two translation initiation elements to initiate translation of each coding region separately to achieve tandem expression of two target polypeptides. In still other alternative embodiments, the circRNA consists of elements arranged in the above order.

In the present disclosure, each coding region independently encodes any type of target polypeptide. The target polypeptides encoded by any two coding regions may be the same or different.

In some alternative embodiments, the circRNA includes an insertion element. The insertion element is ligated to the 5' end of any translation initiation element.

Method and System for Editing Translation Initiation Element Sequence

In some embodiments, the present disclosure provides a method for encoding a translation initiation element, including the following steps:

S1, determining a secondary structure of the translation initiation element according to a translation initiation element sequence.

Specifically, an RNA structure prediction software receives the input translation initiation element sequence and then outputs the secondary structure corresponding to the translation initiation element sequence. In the present disclosure, the software for obtaining the secondary structure of the translation initiation element is not specifically defined, which may be any type of RNA structure prediction software capable of obtaining an RNA secondary structure from an input sequence. Illustratively, the RNA structure prediction software can be at least one of the following: RNAfold, Mfold, RNAfoldweerver, and Vienna RNA.

S2, determining a to-be-edited region in the translation initiation element sequence according to the secondary structure.

In the present disclosure, the to-be-edited region is a position with less hairpin structure, low free energy and easiness for circularization in the secondary structure. In some embodiments, no hairpin structure of more than 20 bp is presented within the range of 100 bp upstream to 100 bp downstream of the to-be-edited region.

By mutating the base of the to-be-edited region at the above position, a nucleic acid recognition site can be inserted into the translation initiation element without affecting sequence activity of the translation initiation element. Also, after mutation of the base site of the to-be-edited region at the above position, effective circularization of circRNA can be achieved.

S3, substituting the base at any one or more than two positions in the to-be-edited region to obtain an editing region including a ribozyme recognition site.

In the present disclosure, the ribozyme recognition site sequence is formed by ligating a nucleotide sequence of the ribozyme recognition site I with a nucleotide sequence of the ribozyme recognition site II.

By substituting the base at any one or more than two positions in the to-be-edited region, a corresponding ribozyme recognition site sequence is formed in the to-be-edited region. Illustratively, the ribozyme recognition site sequence includes, but is not limited to, "5'-TTGGG<u>TCT</u>-3'", "5'-ACGTCT<u>TA</u>ACCAA-3'", "5'-AGGGA<u>TC</u>A-3'", and the like.

Further, the edited translation initiation element sequence is truncated at the position of the ribozyme recognition site to obtain truncated fragment I of the translation initiation element and truncated fragment II of the translational initiation element for constructing a Clean PIE system. Specifically, the position at which the edited translation initiation element sequence is truncated is between two bases of the ribozyme recognition site linked by ribozyme recognition site I to ribozyme recognition site II. For example, when the ribozyme recognition site sequence is "5'-TTGGG<u>TCT</u>-3'", the truncation position is between bases <u>TC</u>.

System for Editing Translation Initiation Element

In some embodiments, the present disclosure provides a system for editing a translation initiation element sequence, wherein the system includes:

a secondary structure constructing module for determining a secondary structure of the translation initiation element according to the translation initiation element sequence;

a to-be-edited region screening module for determining a to-be-edited region in the translation initiation element sequence according to the secondary structure; and a base substitution module for substituting base(s) at any one or two or more positions in the to-be-edited region to obtain an editing region including a ribozyme recognition site.

In the present disclosure, the ribozyme recognition site sequence is formed by ligating the nucleotide sequence of ribozyme recognition site I and the nucleotide sequence of ribozyme recognition site II.

In the present disclosure, the to-be-edited region is a position with less hairpin structure, low free energy and easy for circularization in the secondary structure. In some embodiments, the to-be-edited region does not have a hairpin structure of more than 20 bp within the range of 100 bp upstream to 100 bp downstream.

In addition, the present disclosure also discloses a processing device for screening a target coding region sequence including a ribozyme recognition site, including:

a memory for storing a computer program; and
a processor for executing a computer program to implement the method for editing a translation initiation element sequence as described above.

In addition, the present disclosure also discloses a computer-readable storage medium on which a computer program is stored. When executed by a processor, the computer program implements the method for editing a translation initiation element sequence as described above.

Those skilled in the art will further appreciate that units and algorithm steps described in connection with the embodiments disclosed herein may be implemented with electronic hardware, computer software, or combinations of the two, and that elements and steps of the embodiments have been described above generally in terms of their functions in order to clearly illustrate the interchangeability of hardware and software. Whether such functions are implemented in hardware or software depends upon the particular application and design constraints of the technical solution. Those skilled in the art may implement the described functions in varying ways for each particular application, but such implementation should not be considered to go beyond the scope of the present invention.

EXAMPLES

Other objects, features and advantages of the present disclosure will become apparent from the following detailed description. It should be understood, however, that the detailed description and specific examples, while indicating specific embodiments of the present disclosure, are given for the purpose of illustration only, since various changes and modifications within the spirit and scope of the present disclosure will become apparent to those skilled in the art from this detailed description.

The experimental techniques and methods used in the examples, unless otherwise specified, are conventional techniques and methods. For example, the experimental methods in the following examples, where specific conditions are not specified, are generally in accordance with conventional conditions described in such as Molecular Cloning: A Laboratory Manual (New York: Cold Spring Harbor Laboratory Press, 1989) by Sambrook et al. or the conditions recommended by the manufacturer. The materials, reagents and the like used in the examples can be obtained from regular commercial sources unless otherwise specified.

Example 1

(1) Translation initiation element sequences seq1 (Enterovirus A90 IRES), seq2 (Caprine kobuvirus IRES) and seq3 (Echovirus E29 IRES) with high protein expression verified by previous experiments were selected.

Figure 8:
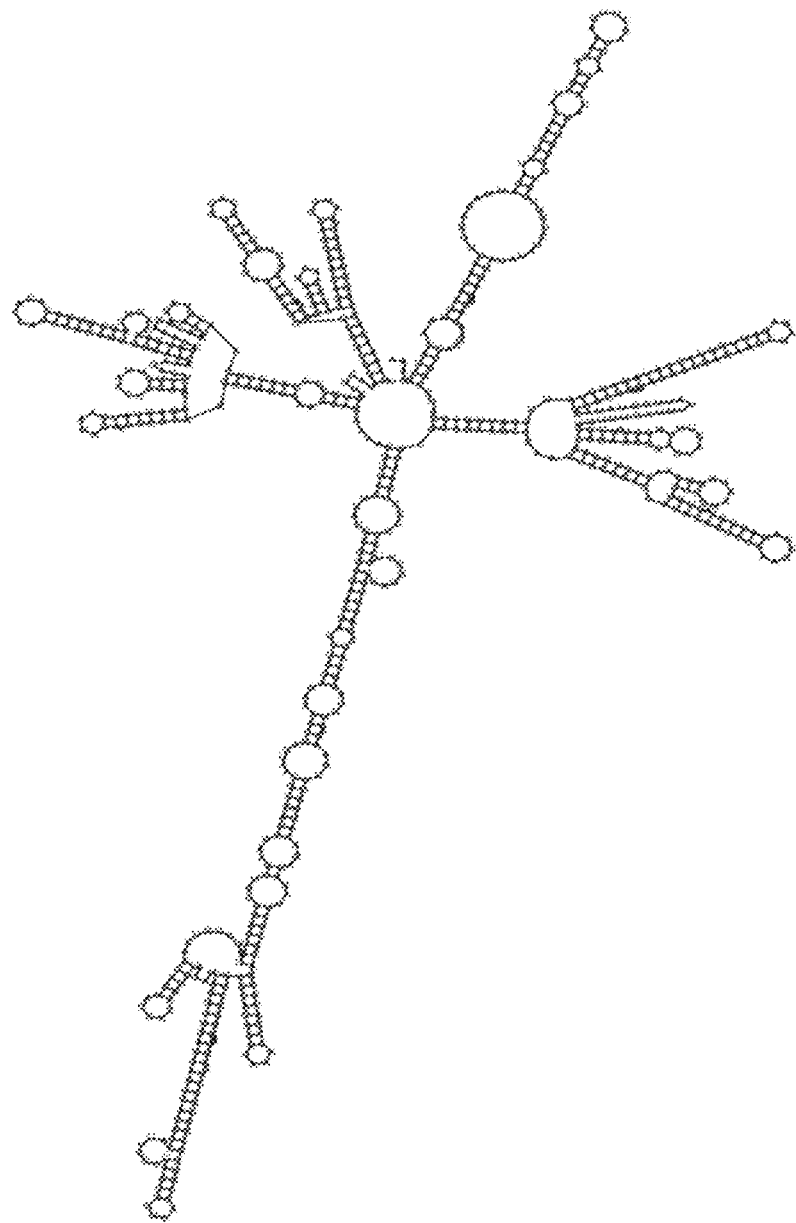
FIG. 8 shows secondary structure prediction results of Enterovirus A90 IRES.
Figure 9:
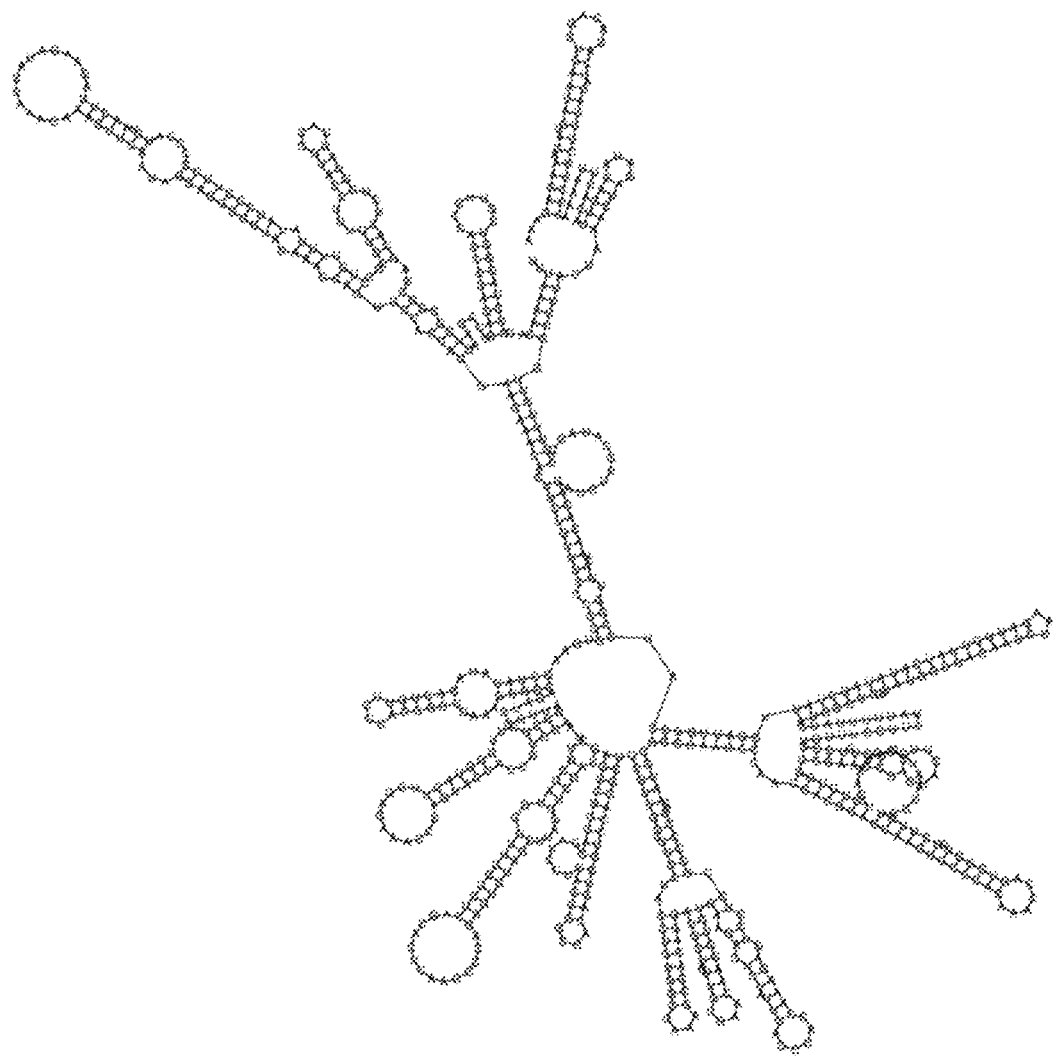
FIG. 9 shows secondary structure prediction results of Caprine kobuvirus IRES.
Figure 10:
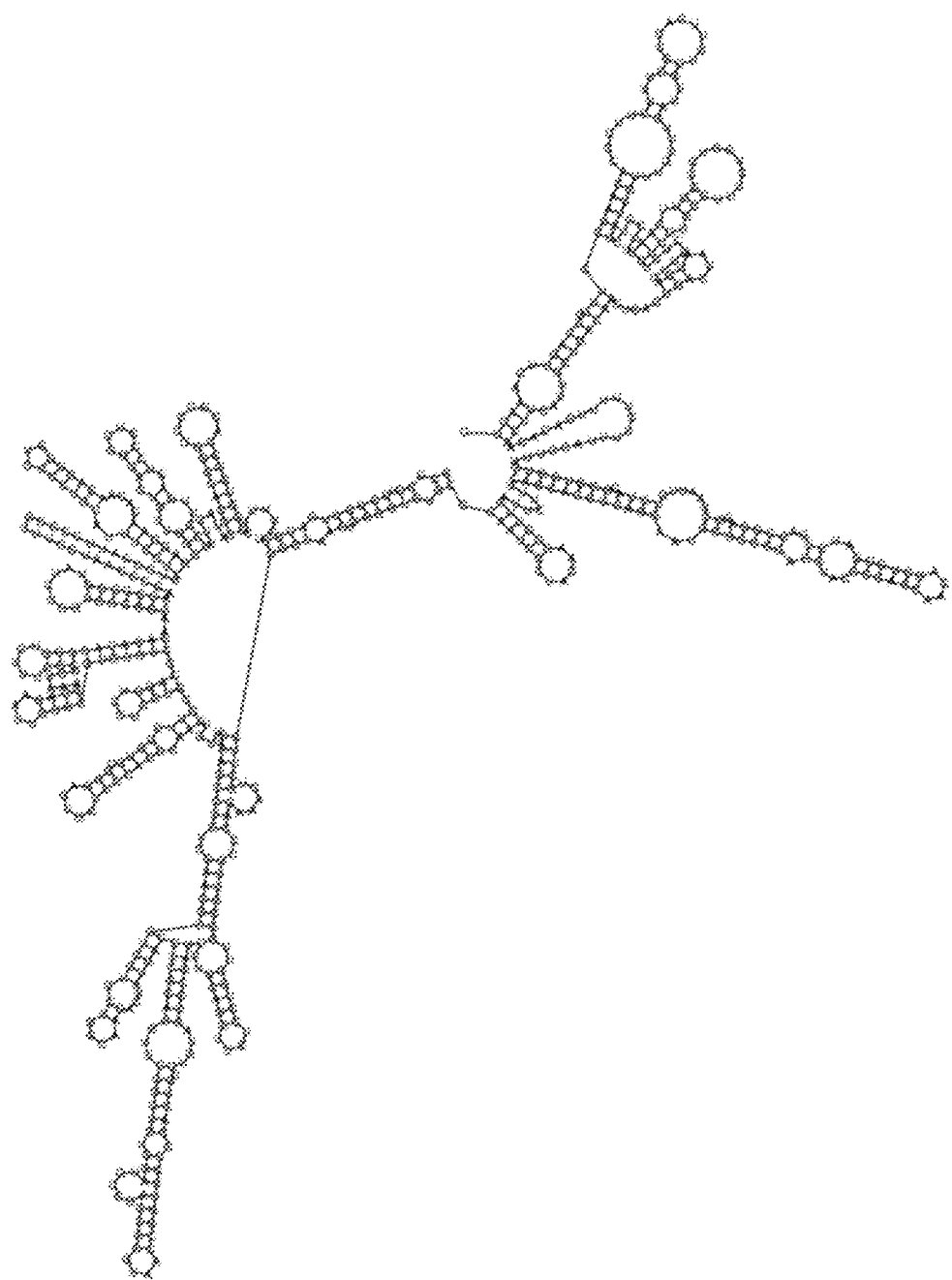
FIG. 10 shows secondary structure prediction results of Echovirus E29 IRES.

(2) Secondary structure predictions were performed on seq1, seq2, and seq3 respectively using software RNAfold, corresponding to FIGS. 8, 9, and 10.

(3) Positions with less hairpin structure (low free energy and easyness for circularization) were selected as to-be-edited regions according to the secondary structure. In particular, no hairpin structure of more than 20 bp is presented within the range of 100 bp upstream and 100 bp downstream of the to-be-edited region. Point mutation was performed on the to-be-edited regions. The seq1 (Enterovirus A90 IRES) sequence has an A-to-T mutation at position 15, a T-to-C mutation at position 20, and a G-to-T mutation at position 21 to obtain a mutated sequence seq4. The seq1 (Enterovirus A90 IRES) sequence has a T-to-G mutation at position 677, and a T-to-C mutation at position 679 to obtain a mutated sequence seq5. The seq2 (Caprine kobuvirus IRES) sequence has a G-to-T mutation at position 80, an A-to-C mutation at position 81, and a G-to-T mutation at position 82 to obtain a mutated sequence seq6. The seq3 (Echovirus E29 IRES) has a G-to-T mutation at position 13, a T-to-C mutation at position 19, and a G-to-T mutation at position 20 to obtain a mutated sequence seq7.

(4) A circularization intermediate consisting of intron fragment II, truncated fragment II of the translational initiation element, a coding region, truncated fragment I of the translation initiation element and intron fragment I in sequence was assembled. The intron fragment II is seq9, the intron fragment I is seq8, and the coding region sequence is a human interleukin-12 sequence (seq10). The truncated fragment II of the translational initiation element resulting from seq4 truncation is seq12, and the truncated fragment I of the translation initiation element resulting from seq4 truncation is seq11. The

TABLE 3

| Reagents | Volume |
| --- | --- |
| 10× Reaction Buffer | 2 μl |
| ATP (20 mM) | 2 μl |
| CTP (20 mM) | 2 μl |
| UTP (20 mM) | 2 μl |
| GTP (20 mM) | 2 μl |
| Linear DNA template | 1 μg |
| T7 RNA Polymerase Mix | 2 μl |
| RNA Nuclease free, H₂O | Total 20 μl |

After incubation at 37° C. for 2.5 hours, the linear DNA template was digested with DNase I. Digestion conditions: 37° C., 15 minutes.

2) Linear mRNA Purification

The transcription products obtained in 1) above were purified by silica membrane spin column (Thermo, GeneJET RNA Purification Kit) method, the OD value was measured, and the size of RNA was determined by 1% denatured agarose gel electrophoresis.

The 1% denatured agarose gel was prepared as follows:
(1) 1 g agarose was weighed into 72 ml nuclease-free H₂O, and heated in a microwave oven for dissolution;
(2) when the agarose was cooled to 55~60° C., 0.1% gel red, 10 ml 10×MOPS, 18 ml formaldehyde were added in a fume cupboard, and gel was filled;
(3) the denatured agarose gel electrophoresis procedure was as follows: equal volume sample of RNA and 2× Loading buffer were taken, and denatured at 65~70° C. for 5 to 10 minutes. Samples were loaded, electrophoresed at 100V for 30 minutes, and photographed with a gel imaging system.

4. mRNA Circularization

1) Circularization Reagent:
GTP Buffer: 50 mM Tris-HCl, 10 mM MgCl2, 1 mM DTT, pH at about 7.5.

2) Circularization System and Conditions:

TABLE 4

| Solutions | Volume |
| --- | --- |
| mRNA | 25 μg mRNA |
| GTP solution(20 mM) | 50 μl |
| GTP buffer | Make up to 500 μl |

The solution was heated at 55° C. for 15 minutes, and then placed on ice. The circularized RNA product was purified by a silica membrane spin column (Thermo, GeneJET RNA Purification Kit) method, the OD value was measured, and the size of RNA was determined by 1% denatured agarose gel electrophoresis.

3) Identification of circRNA by 1% Denatured Agarose Gel

Reagent preparation: 1 g agarose powder was added to 72 ml nuclease-free water, and heated to melt the agarose, adding 10 ml 10×MOPS buffer. 18 ml fresh 37% formaldehyde was then added to the resulting mixture in a fume cupboard, and mixed well. The gel was poured into a tank.

mRNA detection: about 500 ng mRNA solution was added into 2×RNA loading buffer with equal volume, mixed well, and heated at 65° C. for 5 minutes, and subjected to agarose gel detection.

Figure 11:
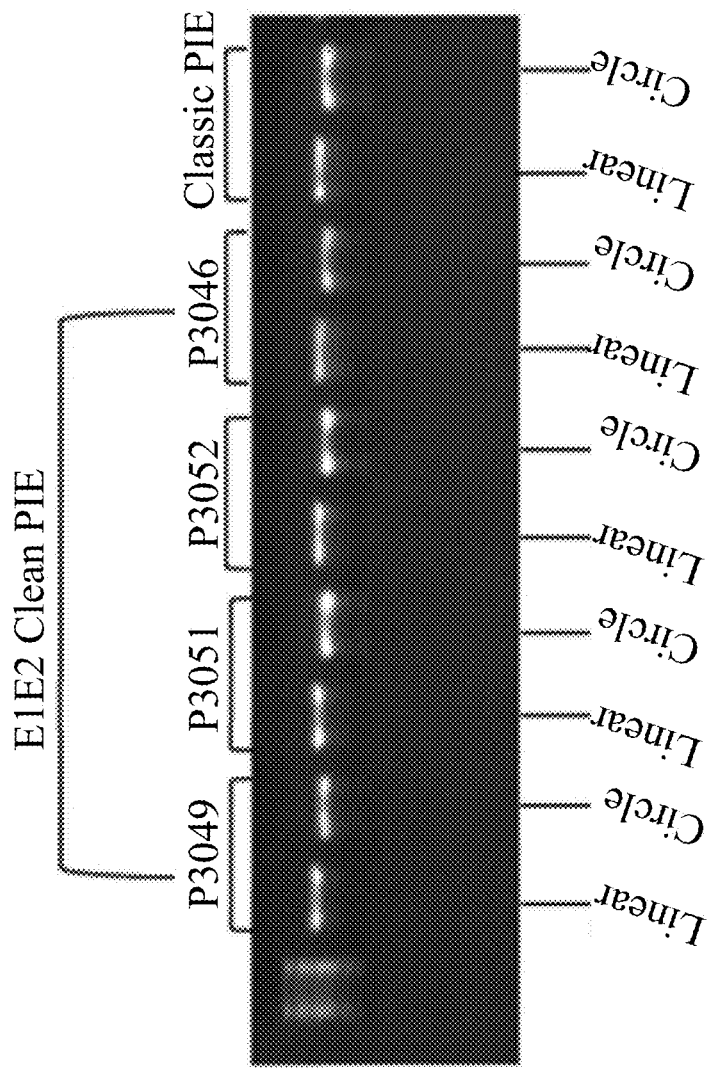
FIG. 11 shows agarose gel electrophoresis detection results of circRNA prepared by the Clean PIE system and a classic PIE system.

The circularization process and method for preparing circRNA using the E1E2 Clean PIE system in the present disclosure did not require any additional modification, and the efficiency of circularization was similar to that of a classic PIE system as detected by agarose gel electrophoresis, and the circularization effect was obvious, without significant difference (FIG. 11).

Example 3: Detection of Immunogenicity after Circularization

Circular mRNA prepared by a classic PIE system and circular mRNAs p3049, p3051, p3052 and p3046 prepared by the E1E2 Clean PIE system of the present disclosure were used to induce the expression of immune response factors in A549 cells. The details are as follows:

Circular mRNA obtained after circularization by a classic PIE system and circular mRNAs p3049, p3051, p3052 and p3046 obtained after circularization by the E1E2 Clean PIE of the present disclosure were subjected to RNaseR digestion followed by HPLC purification, and the resulting purified circular mRNAs were transfected into A549 cells by Lipofectamine Messenger Max (Invitrogen). The specific process is as follows:

A549 cells were inoculated in a DMEM high glucose containing 10% fetal bovine serum and 1% penicillin-streptomycin solution and cultured in 5% CO₂ incubator at 37° C. The cells were subcultured every 2 to 3 days.

(1) Cell transfection:

Before transfection, A549 cells were inoculated in a 24-well plate, 1×10⁵/well, and cultured in a 5% CO₂ incubator at 37° C. After the cells reached 70% to 90% confluency, the mRNA was transfected into 293T cells with 500 ng/well using Lipofectamine MessengerMax (Invitrogen) transfection reagent. The specific operations are as follows:

1) The Messenger MAX™ Reagent was diluted. The dilution system is shown in the table below:

TABLE 5

| Reagents | Volume/well |
| --- | --- |
| MEM serum-free medium | 25 μg |
| Messenger MAX ™ Reagent | 0.75 μl |

The reagents were diluted and mixed, and incubated at room temperature for 5 minutes.

2) The mRNA was diluted. The dilution system is shown in the table below:

TABLE 6

| Reagents | Volume/well |
| --- | --- |
| mRNA | 1 μg |
| MEM serum-free medium | Make up to 25 μl |

3) Mix diluted Messenger MAX™ Reagent and mRNA in a ratio of 1:1

TABLE 7

| Reagents | Volume/well |
| --- | --- |
| Diluted Messenger MAX ™ Reagent | 25 μl |
| Diluted mRNA | 25 μl |

The reagents were diluted and mixed, and incubated at room temperature for 5 minutes.

(2) 50 μl of the above mixture was pipetted and slowly added into a 24-well plate with adhering to the wall, and incubated in 5% CO₂ incubator at 37° C.

(3) Cells expressed for 8 hours were lysed, and the expression level of immune response protein was verified by fluorescent quantitative PCR.

The primer sequences used in fluorescent quantitation PCR are shown below:

```
IFNb-F:
                                    (SEQ ID NO: 21)
TGGGAGGATTCTGCATTACC

IFNb-R:
                                    (SEQ ID NO: 22)
CAGCATCGCTGGTTGAGA

RIG-1-F:
                                    (SEQ ID NO: 23)
CTCCCGGCACAGAAGTGTAT

RIG-1-R:
                                    (SEQ ID NO: 24)
CTTCCTCTGCCTCTGGTTTG

IFNa-F:
                                    (SEQ ID NO: 25)
CCATCTCTGTCCTCCATGAG

IFNa-R:
                                    (SEQ ID NO: 26)
ATTTCTGCTCTGACAACCTC

PKR-F:
                                    (SEQ ID NO: 27)
TGCAAAATGGGACAGAAAGA

PKR-R:
                                    (SEQ ID NO: 28)
TGATTCAGAAGCGAGTGTGC

MDA5-F:
                                    (SEQ ID NO: 29)
ACCAAATACAGGAGCCATGC

MDA5-R:
                                    (SEQ ID NO: 30)
GCGATTTCCTTCTTTTGCAG

TNFa-F:
                                    (SEQ ID NO: 31)
CGTCTCCTACCAGACCAAGG

TNFa-R:
                                    (SEQ ID NO: 32)
CCAAAGTAGACCTGCCCAGA

IL-6-F:
                                    (SEQ ID NO: 33)
TACCCCCAGGAGAAGATTCC
```

-continued

```
IL-6-R:
                                    (SEQ ID NO: 34)
GCCATCTTTGGAAGGTTCAG
```

Figure 12:
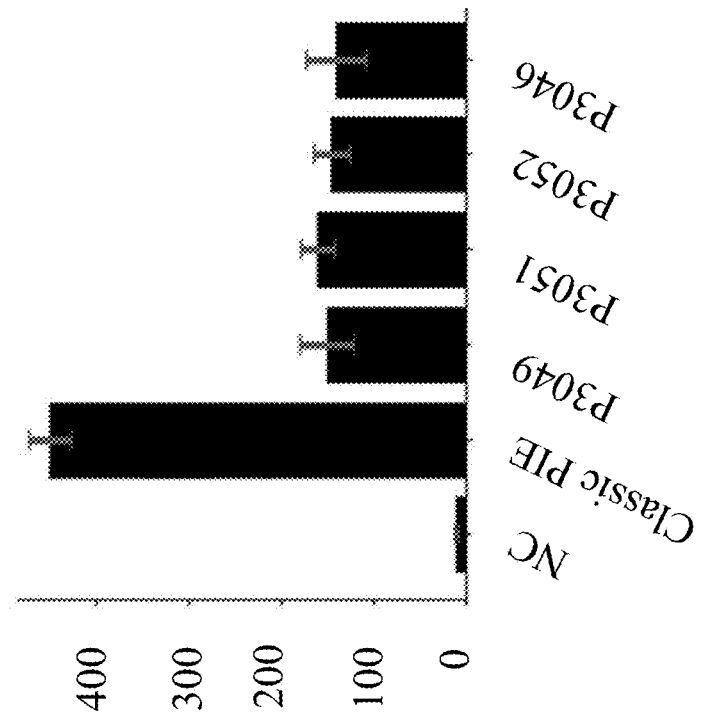
FIG. 12 shows expression results of circular mRNA-induced immune factors prepared using the Clean PIE system and a classic PIE system.

FIG. 12 shows the expression of immune factors induced by circular mRNAs prepared by using the Clean PIE system and a classic PIE system.

The Results Show that:

Although INFb can still cause an immune response after RNase R digestion and HPLC purification in classic PIE, the circular mRNA prepared by the Clean PIE circularization system of the present disclosure is significantly reduced compared with that prepared by the classic PIE, thereby demonstrating that circular mRNA with more accurate sequences can reduce the induction of immunogenicity.

Figure 13:
FIG. 13 shows protein expression results of circular mRNA prepared using the Clean PIE system and a classic PIE system in 293T transfected cells.

Example 4: Verification of In Vitro Expression of Circular mRNA Synthesized In Vitro by the Method of the Present Disclosure In this example, the circular mRNA prepared in Example 2 was transfected into 293T cells, the supernatant was pipetted, and the protein expression level was detected using abeam ab-213791-human IL-12(p70) Elisa kit. Compared with the circular mRNA prepared by a classic PIE circularization method, the circular mRNA prepared by the Clean PIE of the present disclosure had an increased protein expression level in 293T transfected cells (FIG. 13), indicating that the circular mRNA prepared by the Clean PIE in the present disclosure does not introduce additional exon sequences and thus no strong immunogenicity was presented, so that the stability of the circular mRNA in cells was increased. Meanwhile, elisa assay data also shows that circular mRNA prepared by the Clean PIE in the present disclosure showing unexpected improved expression level in vitro compared with circular mRNA prepared by the classic PIE. Based on the above results, the Clean PIE system of the present disclosure can increase the expression level of circular mRNA on the basis of obtaining more accurate circular mRNA.

The above embodiments of the present disclosure are only examples to clearly illustrate the present disclosure, and are not intended for restriction. Those skilled in the art can also make other modifications and variations of different forms in the present invention without departing from the scope or spirit of the present invention. All embodiments need not be, and cannot be, exhaustive. Any modification, equivalent replacement and improvement made in accordance with the spirit and principles of the disclosure shall fall within the protection scope of the claims of the present disclosure.

What is claimed is:

1. A recombinant nucleic acid molecule for preparing a circular RNA, wherein in the 5' to 3' direction, the recombinant nucleic acid molecule comprises elements arranged in the following order:
   an intron fragment II, a truncated fragment II of the translational initiation element, a coding element encoding at least one target polypeptide, a truncated fragment I of the translation initiation element, and an intron fragment I, wherein the truncated fragment II of the translational initiation element comprises the nucleotide sequence of SEQ ID NO: 14, and the truncated fragment I of the translation initiation element comprises the nucleotide sequence of SEQ ID NO: 13;
   wherein the 3' end of the truncated fragment I of the translation initiation element includes ribozyme recognition site I consisting of a first predetermined number of nucleotides located at the 3' end of the truncated fragment I of the translation initiation element;
   the 5' end of the truncated fragment II of the translational initiation element includes a ribozyme recognition site II consisting of a second predetermined number of nucleotides located at the 5' end of the truncated fragment II of the translational initiation element;
   the nucleotide sequence of the truncated fragment I of the translation initiation element and the nucleotide sequence of the truncated fragment II of the translational initiation element are used to form a translation initiation element sequence in the 5' to 3' direction; the nucleotide sequence of the truncated fragment I of the translation initiation element corresponds to a partial sequence of the translation initiation element sequence near the 5' direction, and the nucleotide sequence of the truncated fragment II of the translational initiation element corresponds to a remaining partial sequence of translation initiation element sequence near the 3' direction;
   the nucleotide sequence of the intron fragment I and the nucleotide sequence of the intron fragment II are used to form an intron sequence in the 5' to 3' direction; the nucleotide sequence of intron fragment I includes a partial sequence of the intron sequence near the 5' direction, and the nucleotide sequence of intron fragment II includes the remaining partial sequence of the intron sequence near the 3' direction.

2. The recombinant nucleic acid molecule of claim 1, wherein the intron fragment I and the intron fragment II are derived from Group I intron, the ribozyme recognition site I is derived from a natural exon sequence ligated to the 5' end of the intron fragment I, and the ribozyme recognition site II is derived from a natural exon sequence ligated to the 3' end of the intron fragment II;
   optionally, the Group I intron is derived from any one of the following Group I introns: T4 phage td gene, Anabaena tRNA$^{Leu}$, TpaCOX2, and Ptu.

3. The recombinant nucleic acid molecule of claim 1, wherein the first predetermined number of nucleotides is selected from 3 to 100 nucleotides; or,
   wherein the second predetermined number of nucleotides is selected from 1 to 100 nucleotides; or,
   wherein the sum of the first predetermined number and the second predetermined number is not equal to 3y, y≥1 and y is an integer.

4. The recombinant nucleic acid molecule of claim 1, wherein the translation initiation element sequence is a sequence having an activity of initiating translation of the coding element; and
   optionally, the translation initiation element sequence includes one or a combination of two or more of the following sequences: an IRES sequence, a 5'UTR sequence, a Kozak sequence, a sequence with m$^6$A modification, and a complementary sequence of ribosomal 18S rRNA.

5. The recombinant nucleic acid molecule of claim 1, wherein the coding element comprises at least one coding region; and optionally, the coding element comprises at least two coding regions, and each coding region independently encodes any type of target polypeptide; or,
   the coding element including at least two coding regions, wherein a linker is linked between any two adjacent coding regions; optionally, the linker is a polynucleotide encoding a 2A peptide; or,
   the coding element comprising at least two coding regions, wherein a translation initiation element is ligated between any two adjacent coding regions; optionally, the translation initiation element located between any two adjacent coding regions includes one or a combination of two or more of the following sequences: an IRES sequence, a 5'UTR sequence, a Kozak sequence, a sequence with $m^6A$ modification, and a complementary sequence of ribosomal 18S rRNA.

6. The recombinant nucleic acid molecule of claim 1, wherein the target polypeptide is a human-derived protein or a non-human-derived protein.

7. The recombinant nucleic acid molecule of claim 1, wherein the target polypeptide is selected from one or a combination of two or more of the following: an antigen, an antibody, an antigen-binding fragment, a fluorescent protein, a protein with therapeutic activity against a disease, and a protein with gene editing activity.

8. The recombinant nucleic acid molecule of claim 1, wherein the recombinant nucleic acid molecule further comprises an insertion element between the coding element and the truncated fragment I of the translation initiation element, wherein the insertion element is at least one selected from the group consisting of (i) to (iii): (i) a transcriptional level regulatory element, (ii) a translational level regulatory element, and (iii) a purification element.

9. The recombinant nucleic acid molecule of claim 8, wherein the insertion element includes a sequence of one or a combination of two or more of the following: an untranslated region sequence, a polyA sequence, an aptamer sequence, a riboswitch sequence, and a sequence that binds to a transcriptional regulator.

10. The recombinant nucleic acid molecule of claim 1, wherein the recombinant nucleic acid molecule further comprises a 5' homologous arm and a 3' homologous arm, and the nucleotide sequence of the 5' homologous arm hybridizes to the nucleotide sequence of the 3' homologous arm, wherein the 5' homologous arm is ligated to the 5' end of the intron fragment II, and the 3' homologous arm is ligated to the 3' end of the intron fragment I.

11. The recombinant nucleic acid molecule of claim 1, wherein a nucleotide sequence derived from an exon is not comprised in any one of the intron fragment I, the translation initiation element, or the intron fragment II.

12. The recombinant nucleic acid molecule of claim 1, wherein an exon-derived nucleotide sequence is not included between any two of the intron fragment I, the truncated fragment II of the translational initiation element, the coding element, the truncated fragment I of the translation initiation element and the intron fragment II.

13. A recombinant expression vector comprising the recombinant nucleic acid molecule of claim 1.

14. A method for preparing circular RNA in vitro, comprising the following steps:
    transcription step: transcribing the recombinant nucleic acid molecule of claim 1 to form a precursor nucleic acid molecule;
    circularization step: subjecting the precursor nucleic acid molecule to a circularization reaction to obtain circular RNA; and
    optionally, the method further comprising a step of purifying the circular RNA.

* * * * *

SEQUENCE LISTING

```
Sequence total quantity: 34
SEQ ID NO: 1            moltype = DNA  length = 748
FEATURE                 Location/Qualifiers
misc_feature            1..748
                        note = sequence of IRES
source                  1..748
                        mol_type = other DNA
                        organism = synthetic construct
SEQUENCE: 1
tttaaaacag ctctagggtt gttcccaccc tagaggccca agtggcggct agcactctgg    60
tattacggta cctttgtgcg cctgttttat atcccttccc ccatgtaact tagaagatat   120
taaacaaagt tcaataggag ggggtacaaa ccagtgccac cacgaacaaa cacttctgtt   180
tccccggtga agctacatag actgttccca cggttgaaag tggcagatcc gttatccgct   240
ttggtacttc gagaaaccta gtaccacctt ggaatcttcg atgcgttgcg ctcagcactc   300
aaccccagag tgtagcttag gtcgatgagt ctggacgatc ctcactggcg acagtggtcc   360
aggctgcgtt ggcggcctac ctgtggcgaa agccacagga cgctagttgt gaacaaggtg   420
```

```
tgaagagtct attgagctac caaagagtcc tccggcccct gaatgcggct aatcccaacc  480
acggagcaag tgcccacaaa ccagtgggtg gcttgtcgta atgcgtaagt ctgtggcgga  540
accgactact ttgggtgtcc gtgtttcctt ttatttttat catggctgct tatggtgaca  600
atctaagatt gttatcatat agctattgga ttggccatcc ggtgactaac agagatcttg  660
catacctgtt tgttggtttt actaaactag atatagttac atttaaaact cttctttata  720
tcatacagtt gaatagtaga aagagaaa                                    748

SEQ ID NO: 2              moltype = DNA  length = 665
FEATURE                   Location/Qualifiers
misc_feature              1..665
                          note = sequence of IRES
source                    1..665
                          mol_type = other DNA
                          organism = synthetic construct
SEQUENCE: 2
gcccgtcccc ctcaccctct tttccggtgg ccacgcccgg ccaccgata cttcccttca   60
ctccctcggg actgttgggg aggaacacaa cagggctccc ctgtatttcc tcttcccatt  120
cccccttttcc taacccccaac cgccgtatct ggtggcggta agacacacgg gtctttccct  180
ctaaagcaca attgtgtgtg tgtcccaggt cctcctgcgt tcggtgcggg agtgctccca  240
cccaactgtt gtaagcctgt ccaacgtgtc gtcctggcaa gactatgacg tcgcatgttc  300
cgctgtggat gccgaccggg taaccggttc cccagtgtgt gtagtgcgat cttccaggtt  360
ctcctggttg gcgttgtcca gaaactgctt cgggtaagtg ggtgtgcca aatccctaca  420
agggttgatt cttcaccac cttaggaatg ctccggaggt accccagcaa cagctgggat  480
ctgaccggag gctaattgtc tacgggtggt gtttccattt tctttttcac acaacttcat  540
tgctgacaac tcactgacta atcacttgct ctcttgtgcc tttctgctct ggttcaagtt  600
ccttgattgt ttgtttgatt gcttttcact gctttcttcc cacaatcctt gctcagttca  660
aagtc                                                             665

SEQ ID NO: 3              moltype = DNA  length = 742
FEATURE                   Location/Qualifiers
misc_feature              1..742
                          note = sequence of IRES
source                    1..742
                          mol_type = other DNA
                          organism = synthetic construct
SEQUENCE: 3
ttaaaacagc ctgtgggttg atcccaccca cagggcccac tgggcgctag cactctggta   60
tcacggtacc tttgtgcgcc tgttttatac ttcctccccc aactgcaact tagaagtaac  120
acaaaccgat caacagtcag cgtggcacac cagccacgtt ttgatcaaac acttctgtta  180
ccccggactg agtatcaata gactgctcac gcggttgaag gagaaaacgt tcgttatccg  240
gccaactact tcgagaaacc tagtaacgcc atggaagttg tggagtgttt cgctcagcac  300
taccccagtg tagatcaggt tgatgagtca ccgcattccc cacgggtgac cgtggcggtg  360
gctgcgttgg cggcctgccc atggggaaac ccatgggacg ctcttataca gacatggtgc  420
gaagagtcta ttgagctagt tggtagtcct ccggcccctg aatgcggcta atcccaactg  480
cggagcatac actctcaagc cagagggtag tgtgtcgtaa tgggcaactc tgcagcggaa  540
ccgactactt gggtgtccg tgtttcattt tattcctata ctggctgctt atggtgacaa  600
ttgagagatt gttaccatat agctattgga ttggccatcc ggtgactaac agagctatta  660
tatatctttt tgttgggttt ataccactta gcttgaaaga ggttaaaact ctacattaca  720
ttttaatact gaacaccgca aa                                          742

SEQ ID NO: 4              moltype = DNA  length = 748
FEATURE                   Location/Qualifiers
misc_feature              1..748
                          note = sequence of edited IRES
source                    1..748
                          mol_type = other DNA
                          organism = synthetic construct
SEQUENCE: 4
tttaaaacag ctcttgggtc tttcccaccc tagaggccca agtggcggct agcactctgg   60
tattacggta cctttgtgcg cctgttttat atcccttccc ccatgtaact tagaagatat  120
taaacaaagt tcaataggag ggggtacaaa ccagtgccac cacgaacaaa cacttctgtt  180
tccccggtga agctacatag actgttccca cggttgaaag tggcagatcc gttatccgct  240
ttggtacttc gagaaaccta gtaccacctt ggaatcttcg atgcgttgcg ctcagcactc  300
aacccagag tgtagcttag gtcgatgagt ctggacgatc ctcactgggg acagtggtcc  360
aggctgcgtt ggcggcctac ctgtggcgaa agccacagga cgctagttgt gaacaaggtg  420
tgaagagtct attgagctac caaagagtcc tccggcccct gaatgcggct aatcccaacc  480
acggagcaag tgcccacaaa ccagtgggtg gcttgtcgta atgcgtaagt ctgtggcgga  540
accgactact ttgggtgtcc gtgtttcctt ttatttttat catggctgct tatggtgaca  600
atctaagatt gttatcatat agctattgga ttggccatcc ggtgactaac agagatcttg  660
catacctgtt tgttggtttt actaaactag atatagttac atttaaaact cttctttata  720
tcatacagtt gaatagtaga aagagaaa                                    748

SEQ ID NO: 5              moltype = DNA  length = 748
FEATURE                   Location/Qualifiers
misc_feature              1..748
                          note = sequence of edited IRES
source                    1..748
                          mol_type = other DNA
                          organism = synthetic construct
```

```
SEQUENCE: 5
tttaaaacag ctctagggtt gttcccaccc tagaggccca agtggcggct agcactctgg    60
tattacggta cctttgtgcg cctgttttat atcccttccc ccatgtaact tagaagatat   120
taaacaaagt tcaataggag ggggtacaaa ccagtgccac cacgaacaaa cacttctgtt   180
tccccggtga agctacatag actgttccca cggttgaaag tggcagatcc gttatccgct   240
ttggtacttc gagaaaccta gtaccacctt ggaatcttcg atgcgttgcg ctcagcactc   300
aacccccagag tgtagcttag gtcgatgagt ctggacgatc ctcactgcg acagtggtcc   360
aggctgcgtt ggcggcctac ctgtggcgaa agccacagga cgctagttgt gaacaaggtg   420
tgaagagtct attgagctac caaagagtcc tccggcccct gaatgcggct aatcccaacc   480
acggagcaag tgcccacaaa ccagtgggtg gcttgtcgta atgcgtaagt ctgtggcgga   540
accgactact ttgggtgtcc gtgtttcctt ttatttttat catggctgct tatggtgaca   600
atctaagatt gttatcatat agctattgga ttggccatcc ggtgactaac agagatcttg   660
catacctgtt tgttgggtct actaaactag atatagttac atttaaaact cttctttata   720
tcatacagtt gaatagtaga aagagaaa                                       748

SEQ ID NO: 6               moltype = DNA   length = 665
FEATURE                    Location/Qualifiers
misc_feature               1..665
                           note = sequence of edited IRES
source                     1..665
                           mol_type = other DNA
                           organism = synthetic construct
SEQUENCE: 6
gcccgtcccc ctcaccctct tttccggtgg ccacgcccgg gccaccgata cttcccttca    60
ctccctcggg actgttgggt ctgaacacaa cagggctccc ctgtatttcc tcttcccatt   120
ccccctttcc taaccccaac cgccgtatct ggtggcggta agacacacgg gtctttccct   180
ctaaagcaca attgtgtgtg tgtcccaggt cctcctgcgt tcggtgcggg agtgctccca   240
cccaactgtt gtaagcctgt ccaacgtgtc gtcctggcaa gactatgacg tcgcatgttc   300
cgctgtggat gccgaccggg taaccggttc cccagtgtgt gtagtgcgat cttccaggtt   360
ctcctggttg gcgttgtcca gaaactgctt cgggtaagtg ggtgtgccc aatccctaca   420
agggttgatt ctttcaccac cttaggaatg ctccggaggt accccagcaa cagctgggat   480
ctgaccggag gctaattgtc tacgggtggt gtttccattt tcttttttcac acaacttcat   540
tgctgacaac tcactgacta atcacttgct ctcttgtgcc tttctgctct ggttcaagtt   600
ccttgattgt ttgttgatt gcttttcact gcttcttcc cacaatcctt gctcagttca    660
aagtc                                                                665

SEQ ID NO: 7               moltype = DNA   length = 742
FEATURE                    Location/Qualifiers
misc_feature               1..742
                           note = sequence of edited IRES
source                     1..742
                           mol_type = other DNA
                           organism = synthetic construct
SEQUENCE: 7
ttaaaacagc ctttgggtct atcccaccca cagggcccac tgggcgctag cactctggta    60
tcacggtacc tttgtgcgcc tgttttatac ttcctccccc aactgcaact tagaagtaac   120
acaaaccgat caacagtcag cgtggcacac cagccacgtt ttgatcaaac acttctgtta   180
ccccggactg agtatcaata gactgctcac gcggttgaag gagaaaacgt tcgttatccg   240
gccaactact tcgagaaacc tagtaacgcc atggaagttg tggagtgttt cgctcagcac   300
tacccccagt tagatcaggt tgatgagtca ccgcattccc cacgggtgac cgtggcggtg   360
gctgcgttgg cggcctgccc atggggaaac ccatggacg ctcttataca gacatggtgc   420
gaagagtcta ttgagctagt tggtagtcct ccggcccctg aatgcggcta atcccaactg   480
cggagcatac actctcaagc cagagggtag tgtgtcgtaa tggcaactc tgcagcggaa   540
ccgactactt tgggtgtccg tgtttcattt tattcctata ctggctgctt atggtgacaa   600
ttgagagatt gttaccatat agctattgga ttggccatcc ggtgactaac agagctatta   660
tatatcttttt tgttgggttt ataccactta gcttgaaaga ggtaaaaact ctacattaca   720
ttttaatact gaacaccgca aa                                             742

SEQ ID NO: 8               moltype = DNA   length = 128
FEATURE                    Location/Qualifiers
misc_feature               1..128
                           note = sequence of intron region I
source                     1..128
                           mol_type = other DNA
                           organism = synthetic construct
SEQUENCE: 8
taattgaggc ctgagtataa ggtgacttat acttgtaatc tatctaaacg gggaacctct    60
ctagtagaca atcccgtgct aaattgtagg actaccgtca gttgctcact gtgcatcaga   120
tttctaga                                                             128

SEQ ID NO: 9               moltype = DNA   length = 222
FEATURE                    Location/Qualifiers
misc_feature               1..222
                           note = sequence of intron region II
source                     1..222
                           mol_type = other DNA
                           organism = synthetic construct
SEQUENCE: 9
ggatcctaat acgactcact atagggagac cctcgcacag tgagcaactg acggaggttc    60
```

```
tacataaatg cctaacgact atcccttttgg ggagtagggt caagtgactc gaaacgatag   120
acaacttgct ttaacaagtt ggagatatag tctgctctgc atggtgacat gcagctggat   180
ataattccgg ggtaagatta acgacccttat ctgaacataa tg                     222

SEQ ID NO: 10            moltype = DNA   length = 1626
FEATURE                  Location/Qualifiers
misc_feature             1..1626
                         note = sequence of coding region
source                   1..1626
                         mol_type = other DNA
                         organism = synthetic construct
SEQUENCE: 10
atgtgccacc agcagctggt gatcagctgg ttcagcctgg tgttcctggc cagcccctg    60
gtggccatct gggagctgaa gaaggacgtg tacgtggtgg agctggactg gtaccccgac  120
gcccccggcg agatggtggt gctgacctgc gacacccccg aggaggacgg catcacctgg  180
accctgacc agagcagcga ggtgctgggc agcggcaaga ccctgaccat ccaggtgaag   240
gagttcggcg acgccggcca gtacacctgc acaaggggcg cgaggtgct gagccacagc   300
ctgctgctgc tccacaagaa ggaggacggc atctggagca ccgacatct gaaggaccag   360
aaggagccca gaacaagac cttcctgagg tgcgaggca gaactacag cggcaggttc    420
acctgctggt ggctgaccac catcagcacc gacctgacct tcagcgtgaa gagcagcagg  480
ggcagcagca ccccccaggg cgtgacctgc ggcgctgcca cattgtctgc tgaaagggtt  540
agaggcgaca acaaggagta cgaatacagc gtggagtgcc aggaggacag cgcctgcctgc  600
gccgccgagg agagcctgcc catcgaggtg atggtggacg ccgtgcacaa gctgaagtac   660
gagaactaca ccagcagctt cttcatcagg gacatcatca agcccgaccc tcccaagaac   720
ctgcagctga agccctgaa gaacagcagg caggtggagg tgagctggga gtaccccgac    780
acctgcagca cccctcacag ctacttcagc ctgaccttct gcgtgcaggt ccagggcaag   840
agcaagcggg agaagaagga cagggtgttc accgacaaga ccagcgccac cgtgatctgc   900
aggaagaacg ccagcatcag cgtgagggcc caggacaggt actacagcag cagctggagc   960
gagtgggcca gcgtgccctg cagcggcagc agcggcggcg ggggcagccc cggcggcggc 1020
agcagcagga acctgcccgt ggccaccccc t gatcccgaca tgttcccttg cctgccaccac 1080
agccagaacc tgctgagggc cgtgagcaac atgctgcaga aggccaggca gaccctggaa   1140
ttctaccct gcaccagcga ggagatcgac cacgaggaca tcaccaagga caagaccagc   1200
accgtggagg ccctgtctgc cttggagctg accaagaacg agagctgcct gaacagcagg  1260
gaaaccagct tcatccacca cggcagctgc ctggccagca ggaagaccag cttcatgatg  1320
gccctgtgcc tgagcagcat ctacgaggac ctgaagatgt accaggtgga gttcaagacc  1380
atgaacgcca agctgctgat ggaccccaag aggcagatct tcctggacca gaacatgctg  1440
gccgtgatcg acgagctgat gcaggccctg aacttcaaca gcgaaaccgt gccccagaag  1500
agcagcctgg aggagcccga cttctacaag accaagatca agctgtgcat cctgctgcac  1560
gccttcagga tcagagccgt gaccatcgac agggtgatga gctacctgaa cgccagctga  1620
tgatga                                                             1626

SEQ ID NO: 11            moltype = DNA   length = 19
FEATURE                  Location/Qualifiers
misc_feature             1..19
                         note = sequence of truncated region I from translation
                              Initiationelement
source                   1..19
                         mol_type = other DNA
                         organism = synthetic construct
SEQUENCE: 11
tttaaaacag ctcttgggt                                                19

SEQ ID NO: 12            moltype = DNA   length = 729
FEATURE                  Location/Qualifiers
misc_feature             1..729
                         note = sequence of truncated region II from translation
                              Initiationelement
source                   1..729
                         mol_type = other DNA
                         organism = synthetic construct
SEQUENCE: 12
ctttcccacc ctagaggccc aagtggcggc tagcactctg gtattacggt acctttgtgc    60
gcctgtttta tatcccttcc cccatgtaac ttagaagata ttaaacaaag ttcaatagga   120
ggggtacaa accagtgcca ccacgaacaa acacttctgt ttcccggtg aagctacata    180
gactgttccc acggttgaaa gtggcagatc cgttatccgc tttggtactt cgagaaacct   240
agtaccacct tggaatcttc gatgcgttgc gctcagcact caaccccaga gtgtagctta   300
ggtcgatgag tctggacgat cctcactggc gacagtggtc caggctgcgt tggcggccta   360
cctgtggcga aagccacagg acgctagttg tgaacaaggt gtgaagagtc tattgagcta   420
ccaaagagtc ctccggcccc tgaatgcggc taatcccaac cacggagcaa gtgcccacaa   480
accagtgggt ggcttgtcgt aatgcgtaag tctgtggcgg aaccgactac tttgggtgtc   540
cgtgtttcct tttattttta tcatggctgc ttatggtgac aatctaagat tgttatcata   600
tagctattgg attggccatc cggtgactaa cagagatctt gcatacctgt tgttggtttt   660
tactaaacta gatatagtta catttaaaac tcttctttat atcatacagt tgaatagtag   720
aaagagaaa                                                          729

SEQ ID NO: 13            moltype = DNA   length = 678
FEATURE                  Location/Qualifiers
misc_feature             1..678
                         note = sequence of truncated region I from translation
```

```
                        Initiationelement
source                  1..678
                        mol_type = other DNA
                        organism = synthetic construct
SEQUENCE: 13
tttaaaacag ctctagggtt gttcccaccc tagaggccca agtggcggct agcactctgg    60
tattacggta cctttgtgcg cctgttttat atcccttccc ccatgtaact tagaagatat   120
taaacaaagt tcaataggag ggggtacaaa ccagtgccac cacgaacaaa cacttctgtt   180
tccccggtga agctacatag actgttccca cggttgaaag tggcagatcc gttatccgct   240
ttggtacttc gagaaaccta gtaccacctt ggaatcttcg atgcgttgcg ctcagcactc   300
aaccccagag tgtagcttag gtcgatgagt ctggacgatc ctcactgcg acagtggtcc    360
aggctgcgtt ggcggcctac ctgtggcgaa agccacagga cgctagttgt gaacaaggtg   420
tgaagagtct attgagctac caaagagtcc tccggcccct gaatgcggct aatcccaacc   480
acggagcaag tgcccacaaa ccagtgggtg gcttgtcgta atgcgtaagt ctgtggcgga   540
accgactact ttgggtgtcc gtgtttcctt ttatttttat catggctgct tatggtgaca   600
atctaagatt gttatcatat agctattgga ttggccatcc ggtgactaac agagatcttg   660
catacctgtt tgttgggt                                                 678

SEQ ID NO: 14            moltype = DNA   length = 70
FEATURE                  Location/Qualifiers
misc_feature             1..70
                         note = sequence of truncated region II from translation
                              Initiationelement
source                   1..70
                         mol_type = other DNA
                         organism = synthetic construct
SEQUENCE: 14
ctactaaact agatatagtt acatttaaaa ctcttcttta tatcatacag ttgaatagta    60
gaaagagaaa                                                           70

SEQ ID NO: 15            moltype = DNA   length = 80
FEATURE                  Location/Qualifiers
misc_feature             1..80
                         note = sequence of truncated region I from translation
                              Initiationelement
source                   1..80
                         mol_type = other DNA
                         organism = synthetic construct
SEQUENCE: 15
gcccgtcccc ctcaccctct tttccggtgg ccacgcccgg gccaccgata cttcccttca    60
ctccctcggg actgttgggt                                                80

SEQ ID NO: 16            moltype = DNA   length = 585
FEATURE                  Location/Qualifiers
misc_feature             1..585
                         note = sequence of truncated region II from translation
                              Initiationelement
source                   1..585
                         mol_type = other DNA
                         organism = synthetic construct
SEQUENCE: 16
ctgaacacaa cagggctccc ctgtatttcc tcttcccatt ccccctttcc taacccaac    60
cgccgtatct ggtggcggta agacacacgg gtctttccct ctaaagcaca attgtgtgtg   120
tgtcccaggt cctcctgcgt tcggtgcggg agtgctccca cccaactgtt gtaagcctgt   180
ccaactgtc gtcctggcaa gactatgacg tcgcatgttc cgctgtggat gccgaccggg    240
taaccggttc cccagtgtgt gtagtgcgat cttccaggtt ctcctggttg gcgttgtcca   300
gaaactgctt cgggtaagtg gggtgtgccc aatccctaca agggttgatt cttttcaccac  360
cttaggaatg ctccggaggt accccagcaa cagctgggat ctgaccggag gctaattgtc   420
tacgggtggt gttttccattt tcttttttcac acaacttcat tgctgacaac tcactgacta  480
atcacttgct ctctctgtgcc tttctgctct ggttcaagtt ccttgattgt ttgttttgatt 540
gcttttcact gctttcttcc cacaatcctt gctcagttca aagtc                   585

SEQ ID NO: 17            moltype = DNA   length = 18
FEATURE                  Location/Qualifiers
misc_feature             1..18
                         note = sequence of truncated region I from translation
                              Initiationelement
source                   1..18
                         mol_type = other DNA
                         organism = synthetic construct
SEQUENCE: 17
ttaaaacagc ctttgggt                                                  18

SEQ ID NO: 18            moltype = DNA   length = 724
FEATURE                  Location/Qualifiers
misc_feature             1..724
                         note = sequence of truncated region II from translation
                              Initiationelement
source                   1..724
```

```
                    mol_type = other DNA
                    organism = synthetic construct
SEQUENCE: 18
ctatcccacc cacagggccc actgggcgct agcactctgg tatcacggta cctttgtgcg    60
cctgttttat acttcctccc ccaactgcaa cttagaagta acacaaaacg atcaacagtc   120
agcgtggcac accagccacg ttttgatcaa acacttctgt taccccggac tgagtatcaa   180
tagactgctc acgcggttga aggagaaaac gttcgttatc cggccaacta cttcgagaaa   240
cctagtaacg ccatggaagt tgtggagtgt ttcgctcagc actacccag tgtagatcag    300
gttgatgagt caccgcattc cccacgggtg accgtggcgg tggctgcgtt ggcggcctgc   360
ccatggggaa acccatggga cgctcttata cagacatggt gcgaagagtc tattgagcta   420
gttggtagtc ctccggcccc tgaatgcggc taatcccaac tgcggagcat acactctcaa   480
gccagagggt agtgtgtcgt aatgggcaac tctgcagcgg aaccgactac tttgggtgtc   540
cgtgtttcat tttattccta tactggctgc ttatggtgac aattgagaga ttgttaccat   600
atagctattg gattggccat ccggtgacta acagagctat tatatatctt tttgttgggt   660
ttataccact tagcttgaaa gaggttaaaa ctctacatta cattttaata ctgaacaccg   720
caaa                                                                 724

SEQ ID NO: 19       moltype = DNA  length = 163
FEATURE             Location/Qualifiers
misc_feature        1..163
                    note = sequence of intron region II
source              1..163
                    mol_type = other DNA
                    organism = synthetic construct
SEQUENCE: 19
ctacataaat gcctaacgac tatcccttg gggagtaggg tcaagtgact cgaaacgata     60
gacaacttgc tttaacaagt tggagatata gtctgctctg catggtgaca tgcagctgga   120
tataattccg gggtaagatt aacgacctta tctgaacata atg                     163

SEQ ID NO: 20       moltype = DNA  length = 93
FEATURE             Location/Qualifiers
misc_feature        1..93
                    note = sequence of intron region I
source              1..93
                    mol_type = other DNA
                    organism = synthetic construct
SEQUENCE: 20
taattgaggc ctgagtataa ggtgacttat acttgtaatc tatctaaacg gggaacctct    60
ctagtagaca atcccgtgct aaattgtagg act                                 93

SEQ ID NO: 21       moltype = DNA  length = 20
FEATURE             Location/Qualifiers
misc_feature        1..20
                    note = primer sequence
source              1..20
                    mol_type = other DNA
                    organism = synthetic construct
SEQUENCE: 21
tgggaggatt ctgcattacc                                                20

SEQ ID NO: 22       moltype = DNA  length = 18
FEATURE             Location/Qualifiers
misc_feature        1..18
                    note = primer sequence
source              1..18
                    mol_type = other DNA
                    organism = synthetic construct
SEQUENCE: 22
cagcatcgct ggttgaga                                                  18

SEQ ID NO: 23       moltype = DNA  length = 20
FEATURE             Location/Qualifiers
misc_feature        1..20
                    note = primer sequence
source              1..20
                    mol_type = other DNA
                    organism = synthetic construct
SEQUENCE: 23
ctcccggcac agaagtgtat                                                20

SEQ ID NO: 24       moltype = DNA  length = 20
FEATURE             Location/Qualifiers
misc_feature        1..20
                    note = primer sequence
source              1..20
                    mol_type = other DNA
                    organism = synthetic construct
SEQUENCE: 24
cttcctctgc ctctggtttg                                                20
```

```
SEQ ID NO: 25              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 25
ccatctctgt cctccatgag                                                   20

SEQ ID NO: 26              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 26
atttctgctc tgacaacctc                                                   20

SEQ ID NO: 27              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 27
tgcaaaatgg gacagaaaga                                                   20

SEQ ID NO: 28              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 28
tgattcagaa gcgagtgtgc                                                   20

SEQ ID NO: 29              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 29
accaaataca ggagccatgc                                                   20

SEQ ID NO: 30              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 30
gcgatttcct tcttttgcag                                                   20

SEQ ID NO: 31              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 31
cgtctcctac cagaccaagg                                                   20

SEQ ID NO: 32              moltype = DNA   length = 20
FEATURE                    Location/Qualifiers
misc_feature               1..20
                           note = primer sequence
source                     1..20
                           mol_type = other DNA
                           organism = synthetic construct
SEQUENCE: 32
```

-continued

```
ccaaagtaga cctgcccaga                                                    20

SEQ ID NO: 33          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 33
tacccccagg agaagattcc                                                    20

SEQ ID NO: 34          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 34
gccatctttg gaaggttcag                                                    20
```